US011141370B2

(12) United States Patent
Zhao et al.

(10) Patent No.: US 11,141,370 B2
(45) Date of Patent: Oct. 12, 2021

(54) HAIR COMPOSITIONS COMPRISING A CATIONIC POLYMER MIXTURE AND PROVIDING IMPROVED IN-USE WET FEEL

(71) Applicant: The Procter & Gamble Company, Cincinnati, OH (US)

(72) Inventors: Jean Jianqun Zhao, Cincinnati, OH (US); Eric Michael Hoel, Hamilton, OH (US); Howard David Hutton, III, Oregonia, OH (US); Sarah Elizabeth Mullen, Cincinnati, OH (US); Rootvij Dinesh Patel, Cincinnati, OH (US); Xiaoru Jenny Wang, Mason, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 16/001,053

(22) Filed: Jun. 6, 2018

(65) Prior Publication Data

US 2018/0344612 A1 Dec. 6, 2018

Related U.S. Application Data

(60) Provisional application No. 62/515,920, filed on Jun. 6, 2017.

(51) Int. Cl.
| | | |
|---|---|---|
| *C11D 1/90* | (2006.01) | |
| *A61K 8/73* | (2006.01) | |
| *A61K 8/04* | (2006.01) | |
| *A61Q 5/02* | (2006.01) | |
| *A61K 8/81* | (2006.01) | |
| *A61K 8/89* | (2006.01) | |
| *A61K 8/46* | (2006.01) | |
| *A61K 8/02* | (2006.01) | |
| *A61K 8/892* | (2006.01) | |

(52) U.S. Cl.
CPC ............ *A61K 8/737* (2013.01); *A61K 8/0241* (2013.01); *A61K 8/046* (2013.01); *A61K 8/463* (2013.01); *A61K 8/8176* (2013.01); *A61K 8/89* (2013.01); *A61K 8/892* (2013.01); *A61Q 5/02* (2013.01); *A61K 2800/654* (2013.01)

(58) Field of Classification Search
CPC ......... C11D 1/00; C11D 21/90; C11D 3/0094; C11D 3/162; C11D 3/3742
See application file for complete search history.

(56) References Cited

U.S. PATENT DOCUMENTS

| | | |
|---|---|---|
| 2,879,231 A | 3/1959 | Marshall |
| 3,709,437 A | 1/1973 | Wright |
| 3,950,532 A | 4/1976 | Bouillon et al. |
| 3,959,160 A | 5/1976 | Horsler et al. |
| 4,309,119 A | 1/1982 | Wittersheim |
| 4,329,334 A | 5/1982 | Su et al. |
| 4,726,945 A | 2/1988 | Patel |
| 4,839,166 A | 6/1989 | Grollier et al. |
| 4,867,971 A | 9/1989 | Ryan et al. |
| 4,997,641 A | 3/1991 | Hartnett |
| 5,294,644 A | 3/1994 | Login et al. |
| 5,332,569 A | 7/1994 | Wood et al. |
| 5,364,031 A | 11/1994 | Taniguchi et al. |
| 5,374,421 A | 12/1994 | Tashiro |
| 5,409,695 A | 4/1995 | Abrutyn et al. |
| 5,415,810 A | 5/1995 | Lee et al. |
| 5,417,965 A | 5/1995 | Janchitraponvej et al. |
| 5,439,682 A | 8/1995 | Wivell |
| 5,441,659 A | 8/1995 | Minor |
| 5,560,918 A | 10/1996 | Wivell |
| 5,578,298 A | 11/1996 | Berthiaume |
| 5,599,549 A | 2/1997 | Wivell |
| 5,624,666 A | 4/1997 | Coffindaffer et al. |
| 5,635,469 A | 6/1997 | Fowler et al. |
| 5,747,436 A | 5/1998 | Patel et al. |
| 5,776,444 A | 7/1998 | Birtwistle et al. |
| 5,816,446 A | 10/1998 | Steindorf et al. |
| 5,830,440 A | 11/1998 | Sturla et al. |
| 5,853,618 A | 12/1998 | Barker |
| 5,902,225 A | 5/1999 | Monson |
| 5,925,603 A | 7/1999 | D'Angelo |
| 5,980,877 A | 11/1999 | Baravetto |
| 5,985,939 A | 11/1999 | Minor |
| 6,015,547 A | 1/2000 | Yam |

(Continued)

FOREIGN PATENT DOCUMENTS

| | | |
|---|---|---|
| CA | 2078375 A1 | 3/1994 |
| CN | 102895151 A | 1/2013 |

(Continued)

OTHER PUBLICATIONS

"Natural Detangling Shampoo", Mintel Database, Sep. 13, 2017.
"Soda Shampoo", Mintel Database, Apr. 2015.
"Treatment Foam for Recurrent Scaling Conditions", Mintel Database, Aug. 2007.
All Final and Non-Final Office Actions for U.S. Appl. No. 16/156,045, P&G Case 14975.
All Final and Non-Final Office Actions for U.S. Appl. No. 15/135,657, P&G Case 13809M.
All Final and Non-Final Office Actions for U.S. Appl. No. 15/135,663, P&G Case 13810M.

(Continued)

*Primary Examiner* — Charles I Boyer
(74) *Attorney, Agent, or Firm* — Alexandra S. Anoff

(57) ABSTRACT

A hair care composition. Where the hair care composition contains from about 20% to about 45% detersive surfactant; from about 0.01% to about 2.5% of a cationic synthetic polymer that is a homopolymer and/or a copolymer with charge density from about 2 to about 10 meq/g, and a molecular weight from about 1,000 g/mol to about 2,000,000 g/mol; from about 0.01% to about 2.5%, of a cationic guar polymer with a molecular weight of from about 50,000 g/mol to about 2,500,000 g/mol and charge density from about 0.1 meq/g to about 2.5 meq/g; and from about 0.5% to about 10% silicone.

14 Claims, No Drawings

(56) References Cited

U.S. PATENT DOCUMENTS

| | | |
|---|---|---|
| 6,015,780 A | 1/2000 | Llosas Bigorra et al. |
| 6,020,303 A | 2/2000 | Cripe et al. |
| 6,039,933 A | 3/2000 | Samain et al. |
| 6,046,152 A | 4/2000 | Vinson et al. |
| 6,060,443 A | 5/2000 | Cripe et al. |
| 6,087,309 A | 7/2000 | Vinson et al. |
| 6,110,451 A | 8/2000 | Matz et al. |
| 6,133,222 A | 10/2000 | Vinson et al. |
| 6,153,569 A | 11/2000 | Halloran |
| 6,162,834 A | 12/2000 | Sebillotte-Arnaud et al. |
| 6,231,844 B1 | 5/2001 | Nambu |
| 6,268,431 B1 | 7/2001 | Snyder et al. |
| 6,284,225 B1 | 9/2001 | Bhatt |
| 6,329,331 B1 | 12/2001 | Aronson et al. |
| 6,335,312 B1 | 1/2002 | Coffindaffer et al. |
| 6,423,305 B1 | 7/2002 | Cauwet-Martin et al. |
| 6,451,300 B1 | 9/2002 | Dunlop et al. |
| 6,511,669 B1 | 1/2003 | Garnier |
| 6,565,863 B1 | 5/2003 | Guillou et al. |
| 6,579,907 B1 | 6/2003 | Sebillotte-Arnaud et al. |
| 6,627,585 B1 | 9/2003 | Steer |
| 6,642,194 B2 | 11/2003 | Harrison |
| 6,649,155 B1 | 11/2003 | Dunlop |
| 6,716,455 B2 | 4/2004 | Birkel |
| 6,743,760 B1 | 6/2004 | Hardy et al. |
| 6,827,795 B1 | 12/2004 | Kasturi et al. |
| 6,897,253 B2 | 5/2005 | Schmucker-castner |
| 6,930,078 B2 | 8/2005 | Wells |
| 6,992,054 B2 | 1/2006 | Lee et al. |
| 7,217,752 B2 | 5/2007 | Schmucker-Castner et al. |
| 7,220,408 B2 | 5/2007 | Decoster |
| 7,223,385 B2 | 5/2007 | Gawtrey |
| 7,485,289 B2 | 2/2009 | Gawtrey |
| 7,504,094 B2 | 3/2009 | Decoster |
| 7,531,497 B2 | 5/2009 | Midha et al. |
| 7,541,320 B2 | 6/2009 | Dabkowski et al. |
| 7,659,233 B2 | 2/2010 | Hurley et al. |
| 7,666,825 B2 | 2/2010 | Wagner et al. |
| 7,820,609 B2 | 10/2010 | Soffin et al. |
| 7,829,514 B2 | 11/2010 | Paul et al. |
| 7,928,053 B2 | 4/2011 | Hecht |
| 7,977,288 B2 | 7/2011 | SenGupta |
| 8,084,407 B2 | 12/2011 | Soffin et al. |
| 8,088,721 B2 | 1/2012 | Soffin et al. |
| 8,119,168 B2 | 2/2012 | Johnson |
| 8,124,063 B2 | 2/2012 | Harichian et al. |
| 8,300,949 B2 | 10/2012 | Xu |
| 8,343,469 B2 | 1/2013 | Bierganns et al. |
| 8,388,699 B2 | 3/2013 | Wood |
| 8,401,304 B2 | 3/2013 | Cavallaro et al. |
| 8,435,501 B2 | 5/2013 | Peffly et al. |
| 8,437,556 B1 | 5/2013 | Saisan |
| 8,491,877 B2 | 7/2013 | Schwartz et al. |
| 8,580,725 B2 | 11/2013 | Kuhlman et al. |
| 8,609,600 B2 | 12/2013 | Warr et al. |
| 8,628,760 B2 | 1/2014 | Carter et al. |
| 8,629,095 B2 | 1/2014 | Deleersnyder |
| 8,653,014 B2 | 2/2014 | Hilvert |
| 8,675,919 B2 | 3/2014 | Maladen |
| 8,680,035 B2 | 3/2014 | Kuhlman et al. |
| 8,699,751 B2 | 4/2014 | Maladen |
| 8,709,385 B2 | 4/2014 | Tamarkin |
| 8,741,363 B2 | 6/2014 | Albrecht et al. |
| 8,771,765 B1 | 7/2014 | Fernandez |
| 8,795,635 B2 | 8/2014 | Tamarkin et al. |
| 8,883,698 B2 | 11/2014 | Scheibel et al. |
| 9,006,162 B1 | 4/2015 | Rizk |
| 9,186,642 B2 | 11/2015 | Dihora et al. |
| 9,265,727 B1 | 2/2016 | Lowenborg |
| 9,296,550 B2 | 3/2016 | Smith |
| 9,308,398 B2 | 4/2016 | Hutton et al. |
| 9,428,616 B2 | 8/2016 | Wagner |
| 9,512,275 B2 | 12/2016 | Wagner |
| 9,610,239 B2 | 4/2017 | Feng |
| 9,682,021 B2 | 6/2017 | Tamarkin et al. |
| 9,776,787 B2 | 10/2017 | Nakajima |
| 9,949,901 B2 | 4/2018 | Zhao et al. |
| 9,968,535 B2 | 5/2018 | Kitko |
| 9,968,537 B2 | 5/2018 | Sharma |
| 9,993,419 B2 | 6/2018 | Glenn, Jr. |
| 9,993,420 B2 | 6/2018 | Glenn, Jr. et al. |
| 10,311,575 B2 | 6/2019 | Stofel |
| 10,426,713 B2 | 10/2019 | Song |
| 10,441,519 B2 | 10/2019 | Zhao |
| 10,653,590 B2 | 5/2020 | Torres Rivera |
| 10,799,434 B2 | 10/2020 | Torres Rivera |
| 10,842,720 B2 | 11/2020 | Thompson |
| 10,881,597 B2 | 1/2021 | Lane et al. |
| 10,888,505 B2 | 1/2021 | Johnson |
| 10,912,732 B2 | 2/2021 | Gillis |
| 2001/0000467 A1 | 4/2001 | Murray |
| 2001/0006088 A1 | 7/2001 | Lyle |
| 2001/0006621 A1 | 7/2001 | Coupe et al. |
| 2001/0016565 A1 | 8/2001 | Bodet et al. |
| 2002/0028182 A1 | 3/2002 | Dawson |
| 2002/0037299 A1 | 3/2002 | Turowski-Wanke et al. |
| 2002/0172648 A1 | 11/2002 | Hehner et al. |
| 2002/0193265 A1 | 12/2002 | Perron et al. |
| 2002/0197213 A1 | 12/2002 | Schmenger et al. |
| 2003/0022799 A1 | 1/2003 | Alvarado et al. |
| 2003/0049292 A1 | 3/2003 | Turowski-Wanke et al. |
| 2003/0050150 A1 | 3/2003 | Tanaka |
| 2003/0059377 A1 | 3/2003 | Riley |
| 2003/0083210 A1 | 5/2003 | Goldberg |
| 2003/0108501 A1 | 6/2003 | Hofrichter |
| 2003/0147842 A1 | 8/2003 | Restle |
| 2003/0154561 A1 | 8/2003 | Patel |
| 2003/0161802 A1 | 8/2003 | Flammer |
| 2003/0180246 A1 | 9/2003 | Frantz et al. |
| 2003/0185867 A1 | 10/2003 | Kerschner et al. |
| 2003/0223951 A1 | 12/2003 | Geary et al. |
| 2003/0228272 A1 | 12/2003 | Amjad et al. |
| 2004/0014879 A1 | 1/2004 | Denzer et al. |
| 2004/0144863 A1 | 7/2004 | Kendrick |
| 2004/0229963 A1 | 11/2004 | Stephane |
| 2004/0234484 A1 | 11/2004 | Peffly |
| 2004/0235689 A1 | 11/2004 | Sakai et al. |
| 2005/0020468 A1 | 1/2005 | Frantz et al. |
| 2005/0136011 A1 | 6/2005 | Nekludoff |
| 2005/0152863 A1 | 7/2005 | Brautigam |
| 2005/0201967 A1 | 9/2005 | Albrecht et al. |
| 2005/0202984 A1 | 9/2005 | Schwartz et al. |
| 2005/0233929 A1 | 10/2005 | Queen |
| 2006/0002880 A1 | 1/2006 | Peffly |
| 2006/0030509 A1 | 2/2006 | Modi |
| 2006/0034778 A1 | 2/2006 | Kitano et al. |
| 2006/0057075 A1 | 3/2006 | Arkin et al. |
| 2006/0057097 A1 | 3/2006 | Derici |
| 2006/0079417 A1 | 4/2006 | Wagner |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0090777 A1 | 5/2006 | Hecht |
| 2006/0110415 A1 | 5/2006 | Gupta |
| 2006/0120982 A1 | 6/2006 | Derici et al. |
| 2006/0120988 A1 | 6/2006 | Bailey et al. |
| 2006/0135397 A1 | 6/2006 | Bissey-Beugras |
| 2006/0183662 A1 | 8/2006 | Crotty et al. |
| 2006/0210139 A1 | 9/2006 | Carroll |
| 2006/0229227 A1 | 10/2006 | Goldman |
| 2006/0252662 A1 | 11/2006 | Soffin |
| 2006/0276357 A1 | 12/2006 | Smith, III et al. |
| 2006/0292104 A1 | 12/2006 | Guskey |
| 2007/0072781 A1 | 3/2007 | Soffin et al. |
| 2007/0110700 A1 | 5/2007 | Wells |
| 2007/0154402 A1 | 7/2007 | Trumbore et al. |
| 2007/0155637 A1 | 7/2007 | Smith, III et al. |
| 2007/0160555 A1 | 7/2007 | Staudigel |
| 2007/0179207 A1 | 8/2007 | Fernandez De Castro |
| 2007/0225193 A1 | 9/2007 | Kuhlman et al. |
| 2007/0269397 A1* | 11/2007 | Terada .......... A61K 8/463 424/70.12 |
| 2007/0292380 A1 | 12/2007 | Staudigel |

(56) References Cited

U.S. PATENT DOCUMENTS

| | | |
|---|---|---|
| 2008/0008668 A1 | 1/2008 | Harichian et al. |
| 2008/0019928 A1 | 1/2008 | Franzke |
| 2008/0063618 A1 | 3/2008 | Johnson |
| 2008/0138442 A1 | 6/2008 | Johnson |
| 2008/0152610 A1 | 6/2008 | Cajan |
| 2008/0160093 A1 | 7/2008 | Schwartz et al. |
| 2008/0206179 A1 | 8/2008 | Peffly |
| 2008/0260655 A1 | 10/2008 | Tamarkin et al. |
| 2008/0260665 A1 | 10/2008 | Guerchet et al. |
| 2008/0261844 A1 | 10/2008 | Ruppert et al. |
| 2008/0317698 A1 | 12/2008 | Wells et al. |
| 2009/0029900 A1 | 1/2009 | Cetti et al. |
| 2009/0041702 A1 | 2/2009 | Molenda |
| 2009/0062406 A1 | 3/2009 | Loeffler |
| 2009/0155383 A1 | 6/2009 | Kitko et al. |
| 2009/0178210 A1 | 7/2009 | Bistram |
| 2009/0197784 A1 | 8/2009 | Ainger |
| 2009/0221463 A1 | 9/2009 | Kitko et al. |
| 2009/0246236 A1 | 10/2009 | Kitko |
| 2009/0312224 A1 | 12/2009 | Yang et al. |
| 2009/0324505 A1 | 12/2009 | Seidling |
| 2010/0183539 A1 | 7/2010 | Bernhardt |
| 2010/0310644 A1 | 12/2010 | Liebmann |
| 2011/0008267 A1 | 1/2011 | Arkin et al. |
| 2011/0165107 A1 | 7/2011 | Derks et al. |
| 2011/0171155 A1 | 7/2011 | Federle |
| 2011/0232668 A1 | 9/2011 | Hoffmann et al. |
| 2011/0245126 A1 | 10/2011 | Tsaur et al. |
| 2011/0268778 A1 | 11/2011 | Dihora |
| 2011/0269657 A1 | 11/2011 | Dihora |
| 2011/0305739 A1 | 12/2011 | Royce |
| 2011/0319790 A1 | 12/2011 | Kost et al. |
| 2012/0014901 A1 | 1/2012 | Sunkel et al. |
| 2012/0031419 A1 | 2/2012 | Batt |
| 2012/0034173 A1 | 2/2012 | Batt |
| 2012/0100091 A1 | 4/2012 | Hata et al. |
| 2012/0100092 A1 | 4/2012 | Murray |
| 2012/0291911 A1 | 11/2012 | Smith |
| 2012/0309660 A1 | 12/2012 | Kawasoe |
| 2012/0316095 A1 | 12/2012 | Wei et al. |
| 2013/0034515 A1 | 2/2013 | Stone et al. |
| 2013/0045285 A1 | 2/2013 | Stella et al. |
| 2013/0053295 A1 | 2/2013 | Kinoshita et al. |
| 2013/0053300 A1 | 2/2013 | Scheibel et al. |
| 2013/0089587 A1 | 4/2013 | Staudigel |
| 2013/0115173 A1 | 5/2013 | Trumbore et al. |
| 2013/0143784 A1 | 6/2013 | Rizk |
| 2013/0150338 A1 | 6/2013 | Ananthapadmanabhan |
| 2013/0156712 A1 | 6/2013 | Frantz |
| 2013/0189212 A1 | 7/2013 | Jawale et al. |
| 2013/0211952 A1 | 8/2013 | Sugaya |
| 2013/0216491 A1 | 8/2013 | Ogihara et al. |
| 2013/0243718 A1 | 9/2013 | Pasquet |
| 2013/0244922 A1 | 9/2013 | Bartelt |
| 2013/0280192 A1 | 10/2013 | Carter et al. |
| 2013/0280202 A1 | 10/2013 | Stella et al. |
| 2013/0284195 A1 | 10/2013 | Murdock |
| 2013/0296289 A1 | 11/2013 | Hall et al. |
| 2014/0037703 A1 | 2/2014 | Dihora |
| 2014/0039066 A1 | 2/2014 | Grimadell et al. |
| 2014/0086893 A1 | 3/2014 | Gutmann et al. |
| 2014/0112879 A1 | 4/2014 | Molenda et al. |
| 2014/0127149 A1 | 5/2014 | Lepilleur |
| 2014/0131395 A1 | 5/2014 | Chang |
| 2014/0134125 A1 | 5/2014 | Dahl |
| 2014/0147025 A1 | 5/2014 | Periaswamy |
| 2014/0162979 A1 | 6/2014 | Palla-venkata |
| 2014/0171471 A1 | 6/2014 | Krueger |
| 2014/0216495 A1 | 8/2014 | Bureiko |
| 2014/0228268 A1 | 8/2014 | Fahl et al. |
| 2014/0237732 A1 | 8/2014 | Zuedel Fernandes et al. |
| 2014/0246515 A1 | 9/2014 | Nakajima |
| 2014/0308227 A1 | 10/2014 | Mabille |
| 2014/0309154 A1 | 10/2014 | Carter et al. |
| 2014/0335041 A1* | 11/2014 | Peffly .............. A61K 8/89 424/70.121 |
| 2014/0348884 A1* | 11/2014 | Hilvert .............. A61K 8/891 424/401 |
| 2014/0348886 A1 | 11/2014 | Johnson et al. |
| 2015/0021496 A1 | 1/2015 | Shabbir |
| 2015/0037273 A1 | 2/2015 | Wagner |
| 2015/0050231 A1 | 2/2015 | Murase |
| 2015/0071977 A1 | 3/2015 | Dihora |
| 2015/0093420 A1 | 4/2015 | Snyder |
| 2015/0093429 A1 | 4/2015 | Carter et al. |
| 2015/0098921 A1 | 4/2015 | Franzke et al. |
| 2015/0099684 A1 | 4/2015 | Boutique |
| 2015/0110728 A1 | 4/2015 | Jayaswal |
| 2015/0147286 A1* | 5/2015 | Barrera .............. A61K 8/898 424/70.122 |
| 2015/0218496 A1 | 8/2015 | Schmiedel et al. |
| 2015/0262354 A1 | 9/2015 | Periaswamy |
| 2015/0297489 A1 | 10/2015 | Kleinen |
| 2015/0299400 A1 | 10/2015 | Wagner et al. |
| 2015/0313818 A1 | 11/2015 | Stagg |
| 2015/0359725 A1 | 12/2015 | Glenn, Jr. et al. |
| 2015/0359726 A1 | 12/2015 | Glenn, Jr. et al. |
| 2015/0359728 A1 | 12/2015 | Glenn, Jr. et al. |
| 2016/0008257 A1 | 1/2016 | Zhou et al. |
| 2016/0022566 A1 | 1/2016 | Figura |
| 2016/0113849 A1 | 4/2016 | Grimadell et al. |
| 2016/0128944 A1 | 5/2016 | Chawrai |
| 2016/0193125 A1 | 7/2016 | Jones et al. |
| 2016/0235643 A1 | 8/2016 | Mathonneau et al. |
| 2016/0279048 A1 | 9/2016 | Jayaswal |
| 2016/0287503 A1 | 10/2016 | Schroeder |
| 2016/0287509 A1 | 10/2016 | Peffly |
| 2016/0303043 A1 | 10/2016 | Khoury |
| 2016/0309871 A1 | 10/2016 | Torres Rivera et al. |
| 2016/0310369 A1 | 10/2016 | Thompson et al. |
| 2016/0310370 A1* | 10/2016 | Zhao .............. A61K 8/365 |
| 2016/0310371 A1 | 10/2016 | Zhao |
| 2016/0310375 A1 | 10/2016 | Torres Rivera |
| 2016/0310386 A1 | 10/2016 | Smith, III et al. |
| 2016/0310388 A1 | 10/2016 | Smith, III et al. |
| 2016/0310389 A1 | 10/2016 | Thompson et al. |
| 2016/0310390 A1 | 10/2016 | Smith, III et al. |
| 2016/0310391 A1 | 10/2016 | Smith, III et al. |
| 2016/0310393 A1 | 10/2016 | Chang et al. |
| 2016/0310402 A1 | 10/2016 | Zhao et al. |
| 2016/0317424 A1 | 11/2016 | Kadir |
| 2016/0354300 A1 | 12/2016 | Thompson et al. |
| 2017/0071837 A1 | 3/2017 | Schelges et al. |
| 2017/0101609 A1 | 4/2017 | Vargas |
| 2017/0110690 A1 | 4/2017 | Lamansky et al. |
| 2017/0110695 A1 | 4/2017 | Nishikawa et al. |
| 2017/0165164 A1 | 6/2017 | Zhao et al. |
| 2017/0165165 A1 | 6/2017 | Zhao et al. |
| 2017/0209359 A1 | 7/2017 | Zhao et al. |
| 2017/0239155 A1 | 8/2017 | Hartnett |
| 2017/0252273 A1 | 9/2017 | Renock et al. |
| 2017/0278249 A1 | 9/2017 | Stofel et al. |
| 2017/0283959 A1 | 10/2017 | Shellef |
| 2017/0304172 A1 | 10/2017 | Chang et al. |
| 2017/0304184 A1 | 10/2017 | Glenn, Jr. |
| 2017/0304185 A1 | 10/2017 | Glenn, Jr. et al. |
| 2017/0304186 A1 | 10/2017 | Glenn, Jr. |
| 2017/0333321 A1 | 11/2017 | Carnali |
| 2018/0044097 A1 | 2/2018 | Zeik |
| 2018/0057451 A1 | 3/2018 | Owens et al. |
| 2018/0110594 A1 | 4/2018 | Atkin |
| 2018/0110688 A1 | 4/2018 | Torres Rivera et al. |
| 2018/0110689 A1 | 4/2018 | Torres Rivera et al. |
| 2018/0110690 A1 | 4/2018 | Torres Rivera et al. |
| 2018/0110691 A1 | 4/2018 | Torres Rivera et al. |
| 2018/0110692 A1 | 4/2018 | Torres Rivera et al. |
| 2018/0110693 A1 | 4/2018 | Renock et al. |
| 2018/0110694 A1 | 4/2018 | Renock et al. |
| 2018/0110695 A1 | 4/2018 | Thompson et al. |
| 2018/0110696 A1 | 4/2018 | Johnson et al. |
| 2018/0110704 A1 | 4/2018 | Zhao et al. |
| 2018/0110707 A1 | 4/2018 | Zhao et al. |
| 2018/0110710 A1 | 4/2018 | Zhao et al. |

(56) References Cited

U.S. PATENT DOCUMENTS

| | | | |
|---|---|---|---|
| 2018/0110714 | A1 | 4/2018 | Glenn, Jr. et al. |
| 2018/0116937 | A1 | 5/2018 | Park et al. |
| 2018/0116941 | A1 | 5/2018 | Wang |
| 2018/0221266 | A1 | 8/2018 | Zhao et al. |
| 2018/0256481 | A1 | 9/2018 | Glenn, Jr. |
| 2018/0311135 | A1 | 11/2018 | Chang |
| 2018/0311136 | A1 | 11/2018 | Chang |
| 2018/0318194 | A1 | 11/2018 | Hoffmann et al. |
| 2018/0344611 | A1 | 12/2018 | Zhao et al. |
| 2018/0344612 | A1 | 12/2018 | Zhao et al. |
| 2018/0344613 | A1 | 12/2018 | Zhao et al. |
| 2018/0344614 | A1 | 12/2018 | Zhao et al. |
| 2019/0105242 | A1 | 4/2019 | Song |
| 2019/0105243 | A1 | 4/2019 | Song |
| 2019/0105244 | A1 | 4/2019 | Song |
| 2019/0105245 | A1 | 4/2019 | Song |
| 2019/0105246 | A1 | 4/2019 | Cochran |
| 2019/0105247 | A1 | 4/2019 | Song |
| 2019/0117543 | A1 | 4/2019 | Zhao |
| 2019/0117544 | A1 | 4/2019 | Zhao |
| 2019/0117545 | A1 | 4/2019 | Zhao |
| 2019/0142711 | A1 | 5/2019 | Torres Rivera |
| 2019/0167554 | A1 | 6/2019 | Wankhade |
| 2019/0183777 | A1 | 6/2019 | Gillis |
| 2019/0183778 | A1 | 6/2019 | Glenn, Jr. |
| 2019/0192405 | A1 | 6/2019 | Zhao |
| 2019/0240121 | A1 | 8/2019 | Torres Rivera |
| 2019/0307298 | A1 | 10/2019 | Zhao |
| 2019/0328647 | A1 | 10/2019 | Chang et al. |
| 2019/0365633 | A1 | 12/2019 | Glenn, Jr. |
| 2020/0000690 | A1 | 1/2020 | Renock |
| 2020/0129402 | A1 | 4/2020 | Jamadagni |
| 2020/0163846 | A1 | 5/2020 | Song |
| 2020/0237628 | A1 | 7/2020 | Torres Rivera |
| 2021/0022986 | A1 | 1/2021 | Glenn, Jr. |

FOREIGN PATENT DOCUMENTS

| | | |
|---|---|---|
| CN | 102697668 B | 8/2013 |
| CN | 103356408 A | 10/2013 |
| CN | 102697670 B | 7/2014 |
| CN | 102851015 B | 12/2014 |
| CN | 105726393 A | 7/2016 |
| CN | 105769617 A | 7/2016 |
| CN | 106750361 A | 5/2017 |
| DE | 4315396 A1 | 11/1994 |
| DE | 202005009618 U1 | 9/2005 |
| DE | 102015204987 A1 | 9/2016 |
| EP | 0574086 A2 | 12/1993 |
| EP | 0674898 A2 | 10/1995 |
| EP | 1340485 A2 | 2/2003 |
| EP | 1346720 A2 | 9/2003 |
| EP | 067898 B2 | 3/2006 |
| EP | 1714678 A1 | 10/2006 |
| EP | 2042216 B1 | 9/2015 |
| JP | S56011009 A | 12/1981 |
| JP | 58113300 | 7/1983 |
| JP | 58113300 A | 7/1983 |
| JP | S61236708 A | 10/1986 |
| JP | H04364114 A | 12/1992 |
| JP | 07252134 A | 10/1995 |
| JP | H08310924 A | 11/1996 |
| JP | 09020618 A | 1/1997 |
| JP | 09030938 A | 2/1997 |
| JP | H09175961 A | 7/1997 |
| JP | 2964226 B2 | 10/1999 |
| JP | 3069802 B2 | 7/2000 |
| JP | 2003201217 A | 12/2001 |
| JP | 2002179552 A | 6/2002 |
| JP | 2002226889 A | 8/2002 |
| JP | 2003055699 A | 2/2003 |
| JP | 3480165 B2 | 12/2003 |
| JP | 2005232113 A | 2/2004 |
| JP | 3634988 B2 | 3/2005 |
| JP | 3634991 B2 | 3/2005 |
| JP | 3634996 B2 | 3/2005 |
| JP | 2005187359 A | 7/2005 |
| JP | 2006124312 A | 5/2006 |
| JP | 2006183039 A | 7/2006 |
| JP | 2006193549 A | 7/2006 |
| JP | 2007131687 A | 5/2007 |
| JP | 2008001626 A | 1/2008 |
| JP | 2008214292 A | 9/2008 |
| JP | 2009096778 A | 5/2009 |
| JP | 2011153167 A | 8/2011 |
| JP | 2011190221 A | 9/2011 |
| JP | 5041113 B2 | 7/2012 |
| JP | 2013010757 A | 1/2013 |
| JP | 2013091641 A | 5/2013 |
| JP | 2013151434 A | 8/2013 |
| JP | 5046394 B2 | 1/2014 |
| JP | 2014024875 A | 2/2014 |
| JP | 2014091723 A | 5/2014 |
| JP | 5667790 B2 | 2/2015 |
| JP | 2015101545 A | 6/2015 |
| JP | 2018012673 A | 1/2018 |
| KR | 1020080111280 | 12/2008 |
| KR | 20140060882 A | 5/2014 |
| WO | 9114759 A1 | 10/1991 |
| WO | 91017237 A1 | 11/1991 |
| WO | 9213520 A1 | 8/1992 |
| WO | WO199325650 A1 | 12/1993 |
| WO | WO9502389 A1 | 1/1995 |
| WO | WO9726854 A1 | 7/1997 |
| WO | WO9823258 A1 | 6/1998 |
| WO | WO9918928 A1 | 4/1999 |
| WO | 9924013 A1 | 5/1999 |
| WO | WO9924004 A1 | 5/1999 |
| WO | 9949837 A1 | 10/1999 |
| WO | 0012553 A1 | 3/2000 |
| WO | WO0142409 A1 | 6/2001 |
| WO | WO0148021 A1 | 7/2001 |
| WO | 2004078901 A1 | 9/2004 |
| WO | WO2005023975 A1 | 3/2005 |
| WO | 2008145582 A1 | 12/2008 |
| WO | WO2009016555 A1 | 2/2009 |
| WO | 2009053931 A2 | 4/2009 |
| WO | WO2010052147 A2 | 5/2010 |
| WO | 2012017091 A2 | 2/2012 |
| WO | WO2012055587 A1 | 5/2012 |
| WO | WO2012084970 A1 | 6/2012 |
| WO | WO2013010706 A1 | 1/2013 |
| WO | 2014073245 A1 | 5/2014 |
| WO | WO2014148245 A1 | 9/2014 |
| WO | 2015122371 A1 | 8/2015 |
| WO | WO2016147196 A1 | 9/2016 |
| WO | 2017052161 A1 | 3/2017 |
| WO | 2017140798 A1 | 8/2017 |
| WO | WO2017207685 A1 | 12/2017 |
| WO | WO2018023180 A1 | 2/2018 |

OTHER PUBLICATIONS

All Final and Non-Final Office Actions for U.S. Appl. No. 15/135,677, P&G Case 13811M.

All Final and Non-Final Office Actions for U.S. Appl. No. 15/135,701, P&G Case 13803M.

All Final and Non-Final Office Actions for U.S. Appl. No. 15/135,998, P&G Case 13820M.

All Final and Non-Final Office Actions for U.S. Appl. No. 15/145,696, P&G Case 13802M.

All Final and Non-Final Office Actions for U.S. Appl. No. 15/2788,938, P&G Case 14549M.

All Final and Non-Final Office Actions for U.S. Appl. No. 15/299,860, P&G Case 14324M.

All final and non-final office actions for U.S. Appl. No. 15/379,660 (P&G Case 14177M).

All final and non-final office actions for U.S. Appl. No. 15/379,674 (P&G Case 14177M2).

All final and non-final office actions for U.S. Appl. No. 15/448,911 (P&G Case 14228).

All final and non-final office actions for U.S. Appl. No. 15/467,317 (P&G Case 14211).

(56) References Cited

OTHER PUBLICATIONS

All Final and Non-Final Office Actions for U.S. Appl. No. 15/481,777, (P&G Case 13803MC).
All Final and Non-Final Office Actions for U.S. Appl. No. 15/788,895, P&G Case 14550M2.
All Final and Non-Final Office Actions for U.S. Appl. No. 15/788,949, P&G Case 14550M.
All Final and Non-Final Office Actions for U.S. Appl. No. 15/788,998, P&G Case 14551M.
All Final and Non-Final Office Actions for U.S. Appl. No. 15/789,010, P&G Case 14551M2.
All Final and Non-Final Office Actions for U.S. Appl. No. 15/789,020, P&G Case 14552.
All Final and Non-Final Office Actions for U.S. Appl. No. 15/789,030, P&G Case 14553.
All Final and Non-Final Office Actions for U.S. Appl. No. 15/789,038, P&G Case 14554M.
All Final and Non-Final Office Actions for U.S. Appl. No. 15/789,044, P&G Case 14555M.
All Final and Non-Final Office Actions for U.S. Appl. No. 15/789,081, P&G Case 14556M.
All Final and Non-Final Office Actions for U.S. Appl. No. 15/789,172, P&G Case 14563M.
All Final and Non-Final Office Actions for U.S. Appl. No. 15/789,188, P&G Case 14564M.
All Final and Non-Final Office Actions for U.S. Appl. No. 15/789,208, P&G Case 14565M.
All Final and Non-final Office Actions for U.S. Appl. No. 15/923,499 (P&G Case 13803MC2).
All final and non-final office actions for U.S. Appl. No. 15/962,327 (P&G Case 14788M).
All final and non-final office actions for U.S. Appl. No. 15/962,351, (P&G Case 14789M).
All final and non-final office actions for U.S. Appl. No. 16/001,045 (P&G Case 14845).
All final and non-final office actions for U.S. Appl. No. 16/001,058 (P&G Case 14847).
All final and non-final office actions for U.S. Appl. No. 16/001,064 (P&G Case 14848).
All Final and Non-Final Office Actions for U.S. Appl. No. 16/156,015, P&G Case 14973.
All Final and Non-Final Office Actions for U.S. Appl. No. 16/156,038, P&G Case 14974M.
All Final and Non-Final Office Actions for U.S. Appl. No. 16/156,053, P&G Case 14976M.
All Final and Non-Final Office Actions for U.S. Appl. No. 16/156,066, P&G Case 15365.
All Final and Non-Final Office Actions for U.S. Appl. No. 16/156,072, P&G Case 15367.
All final and non-final office actions for U.S. Appl. No. 16/165,016 (P&G Case 14990).
All final and non-final office actions for U.S. Appl. No. 16/165,033 (P&G Case 14991).
All final and non-final office actions for U.S. Appl. No. 16/165,044 (P&G Case 14992).
All final and non-final office actions for U.S. Appl. No. 16/170,498 (P&G Case 15298M).
All final and non-final office actions for U.S. Appl. No. 16/170,516 (P&G Case 15211M).
All final and non-final office actions for U.S. Appl. No. 16/170,711 (P&G Case 15387).
All final and non-final office actions for U.S. Appl. No. 16/226,914 (P&G Case 15070M).
All final and non-final office actions for U.S. Appl. No. 16/226,927 (P&G Case 15069M).
All final and non-final office actions for U.S. Appl. No. 16/248,900 (P&G Case 14549MC).
All final and non-final office actions for U.S. Appl. No. 16/285,535 (P&G Case 14551M2).
All final and non-final office actions for U.S. Appl. No. 16/376,033 (P&G Case 15190).
All final and non-final office actions for U.S. Appl. No. 16/390,270 (P&G Case 14550M2C).
Anonymous: "MERQUAT Polyquaternium 47 Series, Water Soluble Polymers for Personal Care", Jul. 30, 2017, URL: https://www.in-cosmetics.com/_novadocuments/2729, retrieved on Dec. 21, 2018.
Carbopol Aqua SF-1 Polymer Technical Data Sheet, TDS-294, Dec. 2000.
Christensen et al., "Experimental Determination of Bubble Size Distribution in a WaterColumn by Interferometric Particle Imaging and Telecentric Direct Image Method", Student Report, Aalborg University, Jun. 3, 2014.
Dehyquart Guar: Published Nov. 2010.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018, p. 1.
PCT International Search Report and Written Opinion for PCT/US2016/028728 dated Aug. 5, 2016.
PCT International Search Report and Written Opinion for PCT/US2016/028729 dated Jun. 15, 2016.
PCT International Search Report and Written Opinion for PCT/US2016/028730 dated Aug. 5, 2016.
PCT International Search Report and Written Opinion for PCT/US2016/028735 dated Jul. 25, 2016.
PCT International Search Report and Written Opinion for PCT/US2016/028736 dated Jul. 25, 2016.
PCT International Search Report and Written Opinion for PCT/US2016/028742 dated Jul. 18, 2016.
PCT International Search Report and Written Opinion for PCT/US2016/058123 dated Dec. 21, 2016.
PCT International Search Report and Written Opinion for PCT/US2016/066752 dated Feb. 22, 2017.
PCT International Search Report and Written Opinion for PCT/US2016/066757 dated Feb. 22, 2017.
PCT International Search Report and Written Opinion for PCT/US2017/020604 dated May 11, 2017.
PCT International Search Report and Written Opinion for PCT/US2017/022737 dated Jun. 22, 2017.
PCT International Search Report and Written Opinion for PCT/US2017/057486 dated Jan. 9, 2018.
PCT International Search Report and Written Opinion for PCT/US2017/057487 dated Dec. 19, 2017.
PCT International Search Report and Written Opinion for PCT/US2017/057488 dated Dec. 12, 2017.
PCT International Search Report and Written Opinion for PCT/US2017/057497 dated Jan. 8, 2018.
PCT International Search Report and Written Opinion for PCT/US2017/057503 dated Dec. 13, 2017.
PCT International Search Report and Written Opinion for PCT/US2017/057507 dated Dec. 13, 2017.
PCT International Search Report and Written Opinion for PCT/US2017/057510 dated Jan. 11, 2018.
PCT International Search Report and Written Opinion for PCT/US2017/057511 dated Feb. 2, 2018.
PCT International Search Report and Written Opinion for PCT/US2017/057514 dated Jan. 10, 2018.
PCT International Search Report and Written Opinion for PCT/US2017/057515 dated Dec. 11, 2017.
PCT International Search Report and Written Opinion for PCT/US2017/057522 dated Feb. 2, 2018.
PCT International Search Report and Written Opinion for PCT/US2017/057533 dated Jan. 8, 2018.
PCT International Search Report and Written Opinion for PCT/US2017/057541 dated Dec. 22, 2017.
PCT International Search Report and Written Opinion for PCT/US2018/029313 dated Jul. 11, 2018.
PCT International Search Report and Written Opinion for PCT/US2018/029315 dated Jun. 27, 2018.
PCT International Search Report and Written Opinion for PCT/US2018/036181 dated Aug. 3, 2018.

(56) References Cited

OTHER PUBLICATIONS

PCT International Search Report and Written Opinion for PCT/US2018/036185 dated Aug. 3, 2018.
PCT International Search Report and Written Opinion for PCT/US2018/055102 dated Jan. 9, 2019.
PCT International Search Report and Written Opinion for PCT/US2018/055103 dated Jan. 9, 2019.
PCT International Search Report and Written Opinion for PCT/US2018/055104 dated Jan. 18, 2019.
PCT International Search Report and Written Opinion for PCT/US2018/055105 dated Jan. 8, 2019.
PCT International Search Report and Written Opinion for PCT/US2018/055106 dated Jan. 16, 2019.
PCT International Search Report and Written Opinion for PCT/US2018/055107 dated Jan. 28, 2019.
PCT International Search Report and Written Opinion for PCT/US2018/056669 dated Jan. 31, 2019.
PCT International Search Report and Written Opinion for PCT/US2018/056673 dated Feb. 5, 2019.
PCT International Search Report and Written Opinion for PCT/US2018/056674 dated Feb. 5, 2019.
PCT International Search Report and Written Opinion for PCT/US2018/057451 dated Feb. 25, 2019.
PCT International Search Report and Written Opinion for PCT/US2018/057476 dated Jan. 18, 2019.
PCT International Search Report and Written Opinion for PCT/US2018/066697 dated Mar. 15, 2019.
PCT International Search Report and Written Opinion for PCT/US2018/066701 dated Mar. 15, 2019.
Polyquaternium: "Final Report on the Safety Assessment of the Polyguatemium-10", Journal of the American College of Toxicology, Jan. 1, 1988, URL: http://www.beauty-review.nl/wp-content/uploads/2015/02/Final-Report-on-the Safety-Assessment-of-Polyguaternium-10.pdf, retrieved on Dec. 20, 2018.
Practical Modem Hair Science, Published 2012.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, Nov. 1, 2008, pp. 304-308, p. 305—left-hand column.
"Deep Image Matting", Ning Xu et al, Beckman Institute for Advanced Science and Technology, University of Illinois at Urbana-Champaign, Adobe Research, Mar. 10, 2017.
U.S. Appl. No. 16/170,516, filed Oct. 25, 2018, Chang et al.
U.S. Appl. No. 16/170,711, filed Oct. 25, 2018, Jamadagni et al.
U.S. Appl. No. 16/248,900, filed Jan. 16, 2019, Torres Rivera et al.
U.S. Appl. No. 16/285,535, filed Feb. 26, 2019, Zhao et al.
U.S. Appl. No. 16/226,927, filed Dec. 20, 2018, Glenn, Jr. et al.
U.S. Appl. No. 16/226,914, filed Dec. 20, 2018, Gillis et al.
U.S. Appl. No. 16/376,033, filed Apr. 5, 2019, Zhao et al.
U.S. Appl. No. 16/390,270, filed Apr. 22, 2019, Torres Rivera et al.
All final and non-final office actions for U.S. Appl. No. 16/532,556.
All final and non-final office actions for U.S. Appl. No. 16/846,594.
D'Souza et al., Shampoo and Conditioners: What a Dermatologist Should Know? Indian J Dermatol, May 2015-Jun. 50(3), 248-254 (2015).
Inspection certificate for Hostapon® CCG, Clariant Ibérica Production, S.A., May 6, 2019.
Musazzi, "Emulsion versus nonoemulsion: how much is the formulative shift critical for a cosmetic product?" (Drug Deliv. and Trans. Res. (2018) 8:414-421 (Year 2018).
PCT International Search Report and Written Opinion for PCT/US2019/025923 dated Jun. 24, 2019.
PCT International Search Report and Written Opinion for PCT/US2019/057974 dated Feb. 3, 2020.
Product Bulletin, Amphosol® CG, Cocamidopropyl Betaine, Stepan Company, Jun. 2011.
Product Data Sheet for Chemoryl™LS Surfactant, Sodium Lauroyl Sarcosinate, Lubrizol Advanced Materials, Inc., Mar. 24, 2020.
Product Data Sheet, Eversoft™ UCS-40S, Disodium Cocoyl Glutamate (Sodium Cocoyl Glutamate*), Sino Lion USA, Jul. 2018.
Product Fact Sheet—Hostapon® CCG, mild anionic surfactant for the cosmetic industry, Clariant International Ltd., Aug. 2014.
Product Fact Sheet, Hostapon® CGN, Mild anionic surfactant for the cosmetic industry, Clariant International Ltd., Jan. 2016.
Schaefer, Katie, "Eco-friendly, Non-flammable Liquified Gas Propellant", https://www.cosmeticsandtoiletries.com/formulating/function/aids/138418589.html#close-olyticsmodal. Published Jan. 30, 2012.
UL Prospector® Product Data Sheet, Plantacare® 818 Up, C8-16 fatty alcohol glucoside, BASF, May 21, 2015.
All Final and Non-Final Office Actions for U.S. Appl. No. 15/135,696.
All Final and Non-Final Office Actions for U.S. Appl. No. 15/788,938.
All Final and Non-Final Office Actions for U.S. Appl. No. 15/788,957.
All final and non-final office actions for U.S. Appl. No. 17/071,033.
Fevola, Michael J. "Guar Hydroxypropyltrimonium Chloride." Cosmetics and toiletries 127.1 (2012) 16-21.
Medvedev, Diffusion Coefficients in Multicomponent Mixtures, PhD Thesis from Technical University of Denmark, 2005, 181 pages.
PERM Inc,, Diffusion Coefficient: Measurement Techiques, https://perminc.com/resources/fundamentals-of-fluid-flow-in-porous-media/chapter-3-molecular-diffusion/diffusion-coefficient/measurement-techniques, Oct. 2020.
Robinson et al.. Final Report of the Amended Safety Assessment of Sodium Laureth Sulfate and Related Salts of SulfatedEthoxylated Alcohols, International Journal of Toxicology 29(Supplement 3) 151S-161S, 2010 (Year: 2010).
"Anti-Dandruff Shampoo", Mintel Database, Record No. 752198, dated Aug. 2007 ; pp. 1-3.
"Dandruff Control Shampoo", Mintel Database, Record No. 2300131, dated Jan. 2014; pp. 1-2.
Parchem fine & specialty chemicals. MIPA-laureth sulfate supplier distributor- CAS 83016-76-6; dated 2021; pp. 1-7.

* cited by examiner

HAIR COMPOSITIONS COMPRISING A CATIONIC POLYMER MIXTURE AND PROVIDING IMPROVED IN-USE WET FEEL

FIELD OF THE INVENTION

The present invention relates to hair care compositions. More particularly hair care compositions providing improved in-use wet feel, including hair care compositions that can be delivered in a foam form.

BACKGROUND OF THE INVENTION

Described herein is a hair care composition that enables new product opportunities and consumer benefits by addressing the current disadvantages associated with hair care compositions. In particular, the in-use wet feel for many shampoos, is not optimal. For instance, when using some shampoos, like clarifying shampoos, the final rinse friction is high and many consumers think that their hair feels clean, but complain that the hair does not feel conditioned. On the other hand, other shampoos, including conditioning shampoos, have low final rinse friction and the hair can feel slippery or in some cases slimy and many consumers think that their hair feels conditioned, but not clean.

Also, it can be desirable to deliver hair care compositions, like shampoos, in the form of a foam. Delivery of a hair care composition, including shampoos, in the form of foam represents an attractive consumer concept. One benefit of a shampoo delivered via foam is that it can be readily spread on hair and can enable hair cleansing without leaving significant residue on the hair because the structuring effect of foam enables the use of compositions without polymeric or waxy structurants. However, due to the low density of the foam, it can be desirable to increase the level of surfactant to deliver enough detersive surfactant during each use. This high concentration of surfactant can give the composition a high anionic charge, which can make it difficult to incorporate cationic polymers. Cationic polymers can help form coacervates during use, which can improve the wet feel. It can also be difficult to add a high concentration of cationic polymers because cationic polymers can increase the viscosity of the composition, which can make it difficult for the composition to be delivered via a foam form.

Therefore, there is a need for hair care composition that provide a more optimal in-use wet feel that suggests to the consumer that the hair is both clean and conditioned. It has been found that hair care compositions comprising a combination of a cationic synthetic polymer, such as poly-DADMAC, a cationic guar polymer, and a silicone emulsion can improve the in-use wet feel of hair care compositions, including when the hair care composition is delivered via a foam form.

SUMMARY OF THE INVENTION

In one embodiment, a hair care composition including from about 20% to about 45%, by weight, of a detersive surfactant; from about 0.01% to about 2.5%, by weight, of a cationic synthetic polymer including a homopolymer and/or a copolymer, charge density from about 2 to about 10 meq/g, and a molecular weight from about 1,000 g/mol to about 2,000,000 g/mol; from about 0.01% to about 2.5%, by weight, of a cationic guar polymer with a molecular weight of from about 50,000 g/mol to about 2,500,000 g/mol and charge density from about 0.1 meq/g to about 2.5 meq/g; and from about 0.5% to about 10%, by weight, of silicone wherein the silicone comprises a plurality of particles wherein the average particle size is from about 1 nm to about 500 nm.

In another embodiment, a hair care composition including from about 20% to about 45%, by weight, of a detersive surfactant; from about 0.01% to about 2.5%, by weight, of a cationic synthetic polymer including a homopolymer and/or a copolymer, charge density from about 2 to about 10 meq/g, and a molecular weight from about 1,000 g/mol to about 2,000,000 g/mol; from about 0.01% to about 2.5%, by weight, of a cationic guar polymer with a molecular weight of from about 50,000 g/mol to about 2,500,000 g/mol and charge density from about 0.1 meq/g to about 2.5 meq/g; from about 0.1% to about 8%, by weight, of silicone wherein the silicone has a plurality of particles wherein the average particle size is from about 10 nm to about 500 nm. The hair care composition produces a final rinse friction of from about 1000 gf to about 1700 gf and the hair care composition produces a delta final to initial of at least 125 gf.

DETAILED DESCRIPTION OF THE INVENTION

While the specification concludes with claims particularly pointing out and distinctly claiming the invention, it is believed that the present disclosure will be better understood from the following description.

As used herein, the articles including "a" and "an" when used in a claim, are understood to mean one or more of what is claimed or described.

The term "charge density" as used herein, means the ratio of the number of positive charges on a monomeric unit (of which a polymer is comprised) to the M.Wt. of said monomeric unit. The charge density multiplied by the polymer M.Wt. determines the number of positively charged sites on a given polymer chain. For cationic guars, charge density is measured using standard elemental analysis of percentage nitrogen known to one skilled in the art. This value of percentage nitrogen, corrected for total protein analysis, can then be used to calculate the number or equivalence of positive charges per gram of polymer. For the cationic copolymers, the charge density is a function of the monomers used in the synthesis. Standard NMR techniques know to one skilled in the art would be used to confirm that ratio of cationic and non-ionic monomers in the polymer. This would then be used to calculate the number or equivalence of positive charger per gram of polymer. Once these values are known, the charge density is reported in milliequivalence (meq) per gram of cationic polymer.

As used herein, "comprising" means that other steps and other ingredients which do not affect the end result can be added. This term encompasses the terms "consisting of" and "consisting essentially of".

As used herein, the term "fluid" includes liquids and gels.

As used herein, "mixtures" is meant to include a simple combination of materials and any compounds that may result from their combination.

As used herein, "molecular weight" or "M.Wt." refers to the weight average molecular weight unless otherwise stated. Molecular weight is measured using industry standard method, gel permeation chromatography ("GPC").

As used herein, "personal care composition" includes products such as shampoos, conditioners, conditioning shampoos, shower gels, liquid hand cleansers, hair colorants, facial cleansers, laundry detergent, dish detergent, and other surfactant-based liquid compositions.

As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the hair care composition.

Hair Care Composition

The hair care composition can provide a more optimal in-use wet feel. This can suggest to the consumer that the hair is both clean and conditioned. Compositions with optimal in-use wet feel have relatively low final rinse friction in combination with a relatively high difference between the final to initial friction. It has been found that hair care compositions comprising a combination of a cationic synthetic polymer, such as poly-DADMAC, a cationic guar polymer, and a silicone emulsion, can improve the in-use wet feel of hair care compositions, including when the hair care composition is delivered via a foam form.

The hair care composition can produce a final rinse friction from about 600 gf to about 2000 gf, from about 700 gf to about 1800 gf, from about 800 gf to about 1700 gf, from about 1050 gf to about 1600 gf, from about 1100 gf to about 1500 gf, and/or from about 1150 gf to about 1475 gf. The hair care composition can produce a final rinse friction from about 1025 gf to about 1400 gf. The hair care composition can produce a final rinse friction that is less than 1500 gf, less than 1450 gf, less than 1400 gf, less than 1350 gf, less than 1300 gf, less than 1250 gf, and/or less than 1200 gf.

The hair care composition can produce a delta final to initial (calculated by subtracting the final rinse friction from the initial rinse friction) of from about 100 gf to about 550 gf, from about 150 gf to about 400 gf, from about 175 to about 350 gf, and/or from about 200 gf to about 300 gf. The hair care composition can produce a delta final to initial from about 125 gf to about 280 gf. The hair care composition can produce a delta final to initial of at least at least 125 gf, 150 gf, at least 175 gf, at least 200 gf, at least 225 g, at least 250 gf, and/or at least 275 gf.

The hair care composition may have a liquid phase viscosity of from about 1 centipoise (cP) to about 15,000 cP, from about 10 cP to about 12,000 cP, from about 20 cP to about 10,000 cP, from about 50 cP to about 8,000 cP, from about 100 cP to about 5000 cP, from about 250 cP to about 3000 cP, and/or from about 500 cP to about 2500 cP.

A. Detersive Surfactant

The hair care compositions described herein can include one or more detersive surfactants. The detersive surfactant can be selected from anionic surfactants, amphoteric surfactants, zwitterionic surfactants, and combinations thereof.

The concentration of the detersive surfactant in the composition should be sufficient to provide the desired cleaning and lather performance. The hair care composition can comprise a total detersive surfactant level of from about 20% to about 45%, by weight, from about 25% to about 45%, by weight, and/or from about 25% to about 40%, by weight, from about 30% to about 40%, by weigh, from about 30% to about 35%, by weight. The hair care composition can comprise a total detersive surfactant level of from greater than 15%, greater than 18%, greater than 20%, greater than 22%, and/or greater than 25%, by weight.

The detersive surfactant can comprise an anionic surfactant. Suitable anionic detersive surfactant components for use in the composition herein can include those which are known for use in hair care or other personal care compositions, including shampoos. Suitable anionic surfactants for hair care compositions described herein can include alkyl sulfates and alkyl ether sulfates, water-soluble olefin sulfonates, beta-alkyloxy alkane sulfonates, other sulfonates, succinate surfactants, other sulfonates, and/or other surfactants that are substantially free of sulfates.

The hair care composition may comprise from about 10% to about 40%, from about 15% to about 36%, from about 18% to about 32%, and/or from about 20% to about 28%, by weight, of one or more anionic detersive surfactants.

Anionic surfactants suitable for use herein include alkyl sulfates and alkyl ether sulfates of the formula $ROSO_3M$ and $RO(C_2H_4O)_xSO_3M$, wherein R can be a linear or branched alkyl or alkenyl chain of from about 8 to about 18 carbon atoms, x can be from 1 to 10, and M is a water-soluble cation such as ammonium, sodium, potassium, and triethanolamine cation or salts of the divalent magnesium ion with two anionic surfactant anions. The alkyl ether sulfates may be made as condensation products of ethylene oxide and monohydric alcohols having from about 8 to about 24 carbon atoms. The alcohols can be derived from fats such as coconut oil, palm oil, palm kernel oil, or tallow, or can be synthetic.

TABLE 1

Examples of Typical Alkyl Sulfates and Alky Ether Sulfates

| Surfactant | Supplier | Activity | SLS | SLE1S | SLE2S | SLE3S | SLE > 3S |
|---|---|---|---|---|---|---|---|
| Sodium Lauryl Sulfate | Stepan STEOL SLS | 29% by weight | 100 | 0 | 0 | 0 | 0 |
| Sodium Laureth-1 Sulfate | Stepan STEOL SLES-1 | 26% by weight | 45.5 | 26.3 | 11.8 | 0.07 | 16.33 |
| Sodium Laureth-3 Sulfate | Stepan STEOL SLES-3 | 28% by weight | 18 | 16.7 | 12.6 | 12.4 | 40.30 |

The composition can also include anionic alkyl sulfates and alkyl ether sulfate surfactants having branched alkyl chains which are synthesized from C8 to C18 branched alcohols which may be selected from: Guerbet alcohols, aldol condensation derived alcohols, oxo alcohols and mixtures thereof. Non-limiting examples of the 2-alkyl branched alcohols include oxo alcohols such as 2-methyl-1-undecanol, 2-ethyl-1-decanol, 2-propyl-1-nonanol, 2-butyl 1-octanol, 2-methyl-1-dodecanol, 2-ethyl-1-undecanol, 2-propyl-1-decanol, 2-butyl-1-nonanol, 2-pentyl-1-octanol, 2-pentyl-1-heptanol, and those sold under the tradenames LIAL® (Sasol), ISALCHEM® (Sasol), and NEODOL® (Shell), and Guerbet and aldol condensation derived alcohols such as 2-ethyl-1-hexanol, 2-propyl-1-butanol, 2-butyl-1-octanol, 2-butyl-1-decanol, 2-pentyl-1-nonanol, 2-hexyl-1-octanol, 2-hexyl-1-decanol and those sold under the tradename ISO-FOL® (Sasol) or sold as alcohol ethoxylates and alkoxylates under the tradenames LUTENSOL XP® (BASF) and LUTENSOL XL® (BASF).

The anionic alkyl sulfates and alkyl ether sulfates may also include those synthesized from C8 to C18 branched alcohols derived from butylene or propylene which are sold under the trade names EXXAL™ (Exxon) and Marlipal® (Sasol). This includes anionic surfactants of the subclass of sodium trideceth-n sulfates (STnS), where n is between about 0.5 and about 3.5. Exemplary surfactants of this subclass are sodium trideceth-2 sulfates and sodium trideceth-3 sulfates. The composition can also include sodium tridecyl sulfate.

Suitable surfactants that are substantially free of sulfates can include isethionates, sarcosinates, sulfonates, sulfosuccinates, sulfoacetates, glycinates, glutamates, glucose carboxylates, amphoacetates. taurates, other acyl aminoacids, betaines, sultaines, and/or phosphate esters. Suitable surfactants that are substantially free of sulfates can contain carboxylic acids.

The composition can contain suitable anionic detersive surfactants, which can include water-soluble olefin sulfonates which have the general formula $R^1$—$SO_3M$ where IV is a straight or branched chain, saturated, aliphatic hydrocarbon radical having from 10 to 24 carbon atoms, 10 to 18 carbon atoms, or from 13 to 15 carbon atoms; and M is a water-soluble cation such as ammonium, sodium, potassium, triethanolamine cation, or salts of the divalent magnesium ion with two anionic surfactant anions. Suitable olefin sulfonates such as sodium paraffin sulfonates can be produced through the reaction of $SO_2$ and $O_2$ with a suitable chain length paraffin.

Suitable anionic detersive surfactants can include beta-alkyloxy alkane sulfonates. Beta-alkyloxy alkane sulfonates surfactants conform to Formula I:

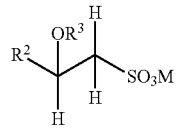

where $R^2$ is a straight chain alkyl group having from about 6 to about 20 carbon atoms, $R^3$ is a lower alkyl group having from about 1 to about 3 carbon atoms, preferably 1 carbon atom, and M is a water-soluble cation as previously described in the water-soluble olefin sulfonates.

Suitable anionic detersive surfactants can include isethionate surfactants. For example, suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride.

Detersive anionic surfactants can be succinate surfactants. Examples of suitable succinate surfactants can include disodium N-octadecylsulfo succinnate, disodium lauryl sulfosuccinate, diammonium lauryl sulfosuccinate, laureth sulfosuccinate, tetrasodium N-(1,2-dicarboxyethyl)-N-octadecylsulfosuccinnate, diamyl ester of sodium sulfosuccinic acid, dihexyl ester of sodium sulfosuccinic acid, and dioctyl esters of sodium sulfosuccinic acid.

Examples of additional anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, sodium lauryl sarcosine, sodium cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth-1 sulfate, sulfate, sodium trideceth-2 sulfate, sulfate, sodium trideceth-3 sulfate, sodium tridecyl sulfate, sodium methyl lauroyl taurate, sodium methyl cocoyl taurate, sodium lauroyl isethionate, sodium cocoyl isethionate ("SCI"), sodium lauroyl methyl isethionate ("SLMI"), sodium laureth sulfosuccinate, sodium lauryl sulfosuccinate, sodium $C_{12}$-$C_{14}$ olefin sulfonate, sodium tridecyl benzene sulfonate, sodium dodecyl benzene sulfonate, sodium lauroyl glycinate, sodium cocoamphoacetate, sodium cocoyl glutamate, sodium lauroyl glutamate, sodium lauryl glucose carboxylate, sodium phosphate ester surfactants, and fatty acid surfactants. and mixtures thereof.

The hair care composition may comprise from about 0% to about 20%, from about 0.5% to about 15%, from about 1% to about 10%, by weight, of one or more co-surfactants selected from the group consisting of amphoteric surfactants, zwitterionic surfactants, non-inonic surfactants, and mixtures thereof. The composition can comprise a co-surfactant selected from the group consisting of: amphoteric surfactants, zwitterionic surfactants, and mixtures thereof. Non-limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Amphoteric surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. The amphoteric surfactant can be selected from the group consisting of: sodium cocaminopropionate, sodium cocaminodipropionate, sodium cocoamphoacetate, sodium cocoamphohydroxypropylsulfonate, sodium cocoamphopropionate, sodium comamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium comamphopropionate, ammonium lauraminopropionate, ammonium lauroamphoacetate, ammonium lauroamphohydroxypropylsulfonate, ammonium lauroamphopropionate, ammonium comamphopropionate, ammonium lauriminodipropionate, triethanolamine cocaminopropionate, triethanolamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine comamphopropionate, triethanonlamine lauriminodipropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and mixtures thereof.

The amphoteric surfactant can be a surfactant according to the following structure:

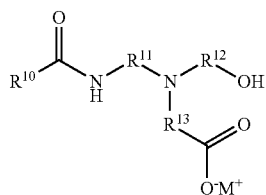

wherein $R^{10}$ is a C-linked monovalent substituent selected from the group consisting of: substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; and wherein $R^{11}$, $R^{12}$, and $R^{13}$ are each independently selected from the group consisting of: C-linked divalent straight alkyl systems comprising 1 to 3 carbon atoms, and C-linked divalent branched alkyl systems comprising 1 to 3 carbon atoms; and wherein M is a monovalent counterion selected from the group consisting of sodium, ammonium and protonated triethanolamine. The amphoteric surfactant is selected from the group consisting of: sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, triethanolamine cocoamphoacetate, and mixtures thereof.

The detersive surfactant system may comprise at least 1%, by weight of the composition, of one or more zwitterionic surfactants which possess a hydroxyl group in their molecular structure. The zwitterionic surfactant can be a derivative of an aliphatic quaternary ammonium, phosphonium, and sulfonium compound, in which the aliphatic radicals are straight or branched chain, and wherein one of the aliphatic substituents contains from about 8 to about 18 carbon atoms and one contains an anionic group such as carboxy, sulfonate, sulfate, phosphate or phosphonate. The zwitterionic surfactant is selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof. The zwitterionic surfactant can be selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

The co-surfactant can be selected from the group consisting of: zwitterionic surfactants, amphoteric surfactants, non-ionic surfactants, and mixtures thereof. The surfactant can be an anionic surfactant and the composition further comprises a co-surfactant, wherein the co-surfactant is selected from the group consisting of: zwitterionic surfactants, amphoteric surfactants, non-ionic surfactants, and mixtures thereof. The cosurfactant can be a non-ionic surfactant selected from the group consisting of: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, and mixtures thereof. The co-surfactant can be a zwitterionic surfactant, wherein the zwitterionic surfactant is selected from the group consisting of: lauryl hydroxysultaine, cocamidopropyl hydroxysultaine, coco-betaine, coco-hydroxysultaine, cocosultaine, lauryl betaine, lauryl sultaine, and mixtures thereof.

B. Cationic Polymers (a) Cationic Guar Polymer

The hair care composition can comprise (a) a cationic guar polymer, wherein the cationic guar polymer can have a weight average M.Wt. of less than about 2.5 million g/mol, and wherein the cationic guar polymer can have a charge density of from about 0.1 meq/g to about 2.5 meq/g.

The composition can comprise from about 0.01% to about 2.2%, from about 0.05% to about 2%, from about 0.1% to about 1.8%, from 0.2% to about 1.6%, from 0.25% to about 1.5%, and/or from 0.3% to about 1.4%, cationic guar polymer, by total weight of the composition. The hair care composition can comprise from about 0.05% to less than 1%, from about 0.05% to about 0.9%, from about 0.1% to about 0.8%, from about 0.2% to about 0.7%, and/or from about 0.2% to about 0.5% of cationic guar polymer, by total weight of the composition. The hair care composition can comprise from about 0.25% to about 1.1%, from about 0.3% to about 0.9%, and/or from about 0.4% to about 0.8% of cationic guar polymer, by total weight of the composition.

Cationic guar polymers are cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

The cationic guar polymer can have a weight average M.Wt. of less than 2.2 million g/mol, or from about 150 thousand g/mol to about 2 million g/mol, or from about 200 thousand to about 1.9 million g/mol, or from about 300 thousand to about 1.8 million g/mol, or from about 400 thousand to about 1.7 million g/mol, and/or from about 500,000 g/mol to about 1.6 million g/mol.

The cationic guar polymer can have a weight average charge density of from about 0.2 meq/g to about 2.2 meg/g, or from about 0.3 meq/g to about 2.0 meg/g, or from about 0.4 meq/g to about 1.9 meg/g, or from about 0.5 meq/g to about 1.8 meg/g, or from about 0.6 meq/g to about 1.7 meg/g, or from about 0.6 meq/g to about 1.5 meq/g, or from about 0.6 meq/g to about 1.3 meg/g, and/or from about 0.7 meq/g to about 1.0 meg/g.

The cationic guar polymer may be formed from quaternary ammonium compounds. The quaternary ammonium compounds for forming the cationic guar polymer can conform to the general formula 1:

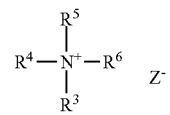

wherein where $R^3$, $R^4$ and $R^5$ are methyl or ethyl groups; $R^6$ is either an epoxyalkyl group of the general formula 2:

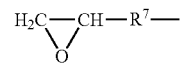

or $R^6$ is a halohydrin group of the general formula 3:

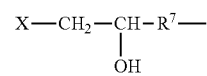

wherein $R^7$ is a $C_1$ to $C_3$ alkylene; X is chlorine or bromine, and Z is an anion such as Cl—, Br—, I— or $HSO_4$—.

The cationic guar polymer can conform to the general formula 4:

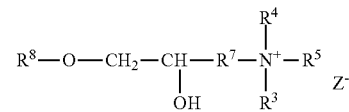

wherein $R^8$ is guar gum; and wherein $R^4$, $R^5$, $R^6$ and $R^7$ are as defined above; and wherein Z is a halogen. The cationic guar polymer can conform to Formula 5:

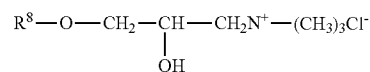

Suitable cationic guar polymers can include cationic guar gum derivatives, such as guar hydroxypropyltrimonium chloride. The cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a molecular weight of 500,000 g/mol. Another guar hydroxypropyltrimonium chloride with a charge density of about 1.1 meq/g and a molecular weight of about 500,000 g/mol is available from Ashland. A further guar hydroxypropyltrimonium chloride with a charge density of about 1.5 meq/g and a molecular weight of about 500,000 g/mole is available from Ashland.

Other suitable guar hydroxypropyltrimonium chloride are: Hi-Care 1000, which has a charge density of about 0.7 meq/g and a Molecular weight of about 600,000 g/mole is available from Rhodia; N-Hance 3269 and N-Hance 3270, which have a charge density of about 0.7 meq/g and a molecular weight of about 425,000 g/mol are available from Ashland; N-Hance 3271 which has a charge density of about 0.7 meq/g and a molecular weight of about 500,000 g/mol and is available from Ashland; BF-13, which is a borate (boron) free guar of charge density of about 1.1 meq/g and molecular weight of about 800,000 and BF-17, which is a borate (boron) free guar of charge density of about 1.7 meq/g and M.W.t of about 800,000 both available from Ashland; N-Hance CG17 has a charge density of about 1.0 meq/g and a molecular weight of about 1,600,000 g/mol and is available from Ashland; and N-Hance 3196 has a charge density of about 0.7 meq/g and a molecular weight of 1,700,000 g/mol and is available from Ashland.

(b) Cationic Synthetic Polymer

The hair care composition can include (b) a cationic synthetic polymer, wherein the cationic synthetic polymer can have a weight average M.Wt. of from about 1,000 g/mol to about 2.0 million g/mol, and wherein the cationic guar polymer can have a charge density of from about 2 meq/g to about 10 meq/g. The hair care composition can comprise a cationic synthetic polymer from about 0.01% to about 2.5% by total weight of the composition.

The cationic synthetic polymers may be formed from
i) one or more cationic monomer units, and optionally
ii) one or more monomer units bearing a negative charge, and/or
iii) a nonionic monomer,
wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and cationic synthetic polymers having the following structure:

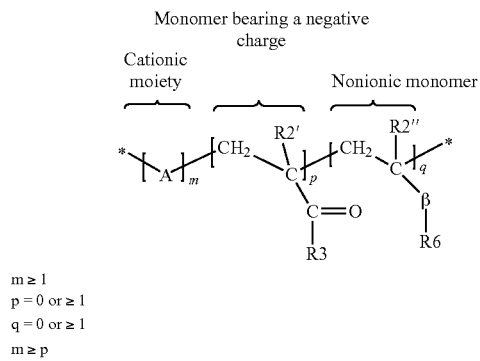

$m \geq 1$
$p = 0$ or $\geq 1$
$q = 0$ or $\geq 1$
$m \geq p$ where A, may be one or more of the following cationic moieties:

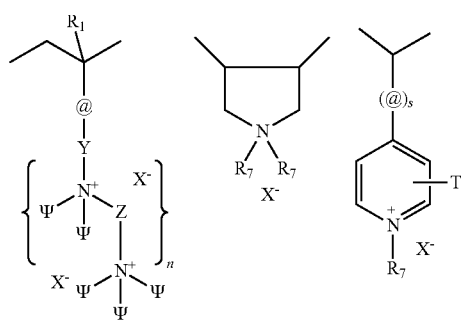

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl arylox;
where Z=C1-C22 alkyl, alkyloxy, aryl or aryloxy;
where R1=H, C1-C4 linear or branched alkyl;
where s=0 or 1, n=0 or $\geq 1$;
where T and R7=C1-C22 alkyl; and
where X-=halogen, hydroxide, alkoxide, sulfate or alkylsulfate.

Where the monomer bearing a negative charge is defined by R2'=H, C1-C4 linear or branched alkyl and R3 as:

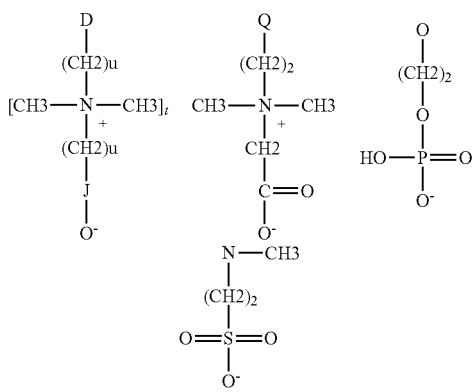

where D=O, N, or S;
where Q=NH$_2$ or O;
where u=1-6;
where t=0-1; and
where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as

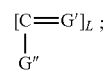

and
where G' and G" are, independently of one another, O, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyl-dialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula —NR$_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X-) in association with the cationic synthetic polymers may be any known counterion so long as the polymers remain soluble or dispersible in water, in the hair care composition, or in a coacervate phase of the hair care composition, and so long as the counterions are physically and chemically compatible with the essential components of the hair care composition or do not otherwise unduly impair product performance, stability or aesthetics.

Non limiting examples of such counterions include halides (e.g., chlorine, fluorine, bromine, iodine), sulfate and methylsulfate.

The cationic synthetic polymer can have a weight average M.Wt. of from about 1,500 g/mol to about 1.8 million g/mol, or from about 2,000 g/mol to about 1.7 million g/mol, or from about 3,000 g/mol to about 1.6 million g/mol, or from about 4,000 g/mol to about 1.5 million g/mol, or from about 5,000 g/mol to about 1.6 million g/mol, or from about 6,000 g/mol to about 1.5 million g/mol, or from about 7,000 g/mol to about 1.4 million g/mol, or from about 8,000 g/mol to about 1.4 million g/mol, or from about 9,000 g/mol to about 1.3 million g/mol, or from about 10,000 g/mol to about 1.2 million g/mol or from about 11,000 g/mol to about 1.1 million g/mol, or from about 25,000 g/mol to about 750,000 g/mol, or from about 50,000 g/mol to about 500,000 g/mol, or from about 75,000 g/mol to about 300,000 g/mol, and/or from about 100,000 g/mol to about 200,000 g/mol.

The cationic synthetic polymer can have a weight average charge density of from about 2.2 meq/g to about 9.5 meg/g, or from about 2.5 meq/g to about 8 meg/g, or from about 3 meq/g to about 8 meg/g, or from about 3.5 meq/g to about 7.5 meg/g, and/or from about 4 meq/g to about 7 meg/g.

The composition can comprise a cationic synthetic polymer from about 0.05% to about 2.2%, or from about 0.05% to about 2%, or from about 0.1% to about 1.8%, or from about 0.1% to about 1.6%, or from about 0.15% to about 1.5%, or from about 0.15% to about 1.4%, from about 0.2% to about 1.3%, or from about 0.2% to about 1.2%, from about 0.2% to about 1%, and/or from 0.2% to 0.8%, by total weight of the composition.

The cationic synthetic polymer can comprise polydiallyldimethylammonium chloride (polyDADMAC). PolyDADMAC is also known as polyquaternium-6. Specific examples of polyDADMAC are Mirapol® 100 series from Solvay, Merquat™ 100 series from Lubrizol and Salcare® SC 30 from BASF. For example, Mirapol® 100s has a charge density of 6.2 meq/g and a molecular weight of 150,000 g/mol, is available from Solvay.

The hair care composition may further comprise (c) a cationic non-guar galactomannan polymer, (d) a cationic starch polymer, (e) a cationic copolymer of acrylamide monomers and cationic monomers, (f) a cationic cellulose polymer or (g) a mixture of such polymers (c) Cationic Non-Guar Galactomannan Polymers The dispersion compositions can comprise a galactomannan polymer derivative having a mannose to galactose ratio of between 5:1 and 1:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and also is affected by climate. Non Guar Galactomannan polymer derivatives can have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and *Cassia* gum (5 parts mannose/1 part galactose).

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

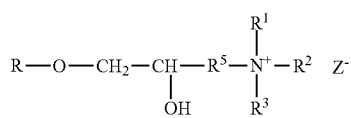

wherein R is the gum. The cationic galactomannan derivative can be a gum hydroxypropyltrimethylammonium chloride, which can be more specifically represented by the general formula 7:

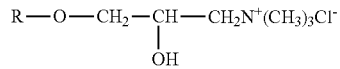

The galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose that is greater than about 4:1. The dispersion compositions may comprise a galactomannan polymer derivative by weight of the composition. The hair care compositions can comprise from about 0.05% to about 2%, by weight of the composition, of a galactomannan polymer derivative.

(d) Cationically Modified Starch Polymer

The dispersion compositions may comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The dispersion compositions can comprise cationically modified starch polymers at a range of about 0.01% to about 10%, and/or from about 0.05% to about 5%, by weight of the composition.

The cationically modified starch polymers disclosed herein can have a percent of bound nitrogen of from about 0.5% to about 4%.

The dispersion compositions may include starch polymers that is chemically modified by the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers can generally have a degree of substitution of a cationic group from about 0.1 to about 7. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof.

Cationically modified starch polymers can be selected from degraded cationic maize starch, cationic tapioca, cationic potato starch, and mixtures thereof.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance.gtoreq.80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in compositions is available from known starch suppliers. Nonionic modified starch that could be further derivatized to a cationically modified starch as is known in the art can be suitable for use. Other suitable modified starch starting materials may be quaternized, as is known in the art, to produce the cationically modified starch polymer suitable for use in the invention.

Starch Degradation Procedure: A starch slurry is prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

(e) Cationic Copolymer of an Acrylamide Monomer and a Cationic Monomer

The dispersion composition can comprise a cationic copolymer of an acrylamide monomer and a cationic monomer. The cationic copolymer can be a synthetic cationic copolymer of acrylamide monomers and cationic monomers.

The cationic copolymer can comprise:

(i) an acrylamide monomer of the following Formula AM:

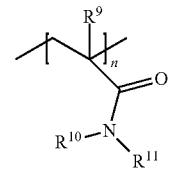

Formula AM where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula CM:

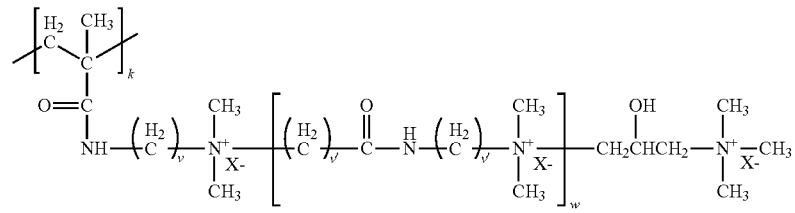

Formula CM where k=1, each of v, v', and v" is independently an integer of from 1 to 6, w is zero or an integer of from 1 to 10, and $X^-$ is an anion.

The cationic monomer can conform to Formula CM and where k=1, v=3 and w=0, z=1 and $X^-$ is $Cl^-$ to form the following structure:

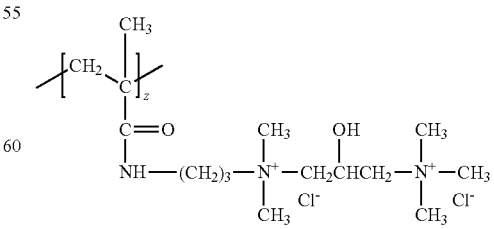

The above structure may be referred to as diquat. The cationic monomer can conform to Formula CM and wherein v and v" are each 3, v'=1, w=1, y=1 and $X^-$ is $Cl^-$, such as:

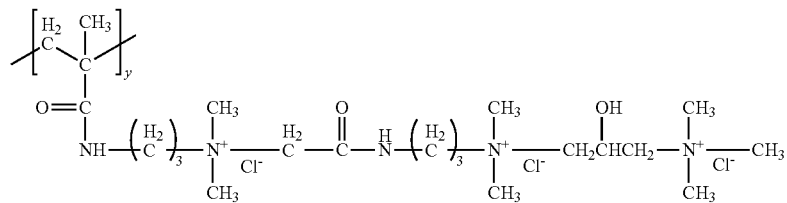

The above structure may be referred to as triquat.

The acrylamide monomer can be either acrylamide or methacrylamide.

The cationic copolymer (b) can be AM:TRIQUAT which is a copolymer of acrylamide and 1,3-Propanediaminium, N-[2-[[[dimethyl[3-[(2-methyl-1-oxo-2-propenyl)amino] propyl]ammonio]acetyl]amino]ethyl]2-hydroxy-N,N,N',N', N'-pentamethyl-, trichloride. AM:TRIQUAT is also known as polyquaternium 76 (PQ76). AM:TRIQUAT may have a charge density of 1.6 meq/g and a M.Wt. of 1.1 million g/mol.

The cationic copolymer can be an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer comprises a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be water-soluble. The cationic copolymer can be formed from (1) copolymers of (meth)acrylamide and cationic monomers based on (meth) acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. Cationized esters of the (meth)acrylic acid containing a quaternized N atom can be quaternized dialkylaminoalkyl (meth)acrylates with C1 to C3 in the alkyl and alkylene groups. The cationized esters of the (meth) acrylic acid containing a quaternized N atom are selected from the group consisting of: ammonium salts of dimethylaminomethyl (meth)acrylate, dimethylaminoethyl (meth) acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. The cationized esters of the (meth)acrylic acid containing a quaternized N atom can be dimethylaminoethyl acrylate, which may be quaternized with an alkyl halide, or with methyl chloride or benzyl chloride or dimethyl sulfate (ADAME-Quat). The cationic monomer when based on (meth)acrylamides can be quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

The cationic monomer based on a (meth)acrylamide is a quaternized dialkylaminoalkyl(meth)acrylamide with C1 to C3 in the alkyl and alkylene groups. The cationic monomer based on a (meth)acrylamide is dimethylaminopropylacrylamide, which is quaternized with an alkyl halide, especially methyl chloride or benzyl chloride or dimethyl sulfate.

The cationic monomer is a hydrolysis-stable cationic monomer. Hydrolysis-stable cationic monomers can be, in addition to a dialkylaminoalkyl(meth)acrylamide, all monomers that can be regarded as stable to the OECD hydrolysis test. The cationic monomer is hydrolysis-stable and the hydrolysis-stable cationic monomer is selected from the group consisting of: diallyldimethylammonium chloride and water-soluble, cationic styrene derivatives.

The cationic copolymer is a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer is formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer is a trimethylammoniopropylmethacrylamide chloride-N-Acrylamide copolymer, which is also known as AM:MAPTAC. AM:MAPTAC may have a charge density of about 1.3 meq/g and a M.Wt. of about 1.1 million g/mol. The cationic copolymer is AM:ATPAC. AM:ATPAC may have a charge density of about 1.8 meq/g and a M.Wt. of about 1.1 million g/mol.

(f) Cationic Cellulose Polymers

Suitable cationic cellulose polymers are salts of hydroxyethyl cellulose reacted with trimethyl ammonium substituted epoxide, referred to in the industry (CTFA) as Polyquaternium 10 and available from Dwo/Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

C. Silicone Emulsions

The hair care composition can comprise from about 0% to about 20%, from about 0.5% to about 18%, from about 1% to about 16%, from about 1.5% to about 14%, from about 1.5% to about 12%, from about 1.5% to about 10%, from about 1.5% to about 8%, and/or from about 1.5% to about 6%, by weight, of one of more silicone polymers. The silicone polymer can be added into the hair care composition as an aqueous pre-emulsion. The silicone pre-emulsion can comprise one or more silicone polymers and an emulsifying system. The silicone polymer content in the silicone pre-emulsion can be from about 10%, by weight, to about 70%, by weight, or about 15%, by weight, to about 60%, by weight, or from about 18%, by weight, to about 50% by weight.

The silicone emulsion can have an average particle size of less than 500 nm, alternatively 300 nm, alternatively less than about 200 nm, and alternatively less than about 100 nm. The silicone emulsion can have an average particle size of from about 5 nm to about 500 nm, from about 10-nm to about 400 nm, and/or from about 20 nm to about 300 nm. The silicone emulsion can be in the form of a nano-emulsion.

The particle size of the one or more silicones may be measured by dynamic light scattering (DLS). A Malvern Zetasizer Nano ZEN3600 system using He—Ne laser 633 nm may be used for the measurement at 25° C.

The autocorrelation function may be analyzed using the Zetasizer Software provided by Malvern Instruments, which determines the effective hydrodynamic radius, using the Stokes-Einstein equation:

$$D = \frac{k_B T}{6\pi \eta R}$$

wherein $k_B$ is the Boltzmann Constant, T is the absolute temperature, $\eta$ is the viscosity of the medium, D is the mean diffusion coefficient of the scattering species, and R is the hydrodynamic radius of particles.

Particle size (i.e. hydrodynamic radius) may be obtained by correlating the observed speckle pattern that arises due to Brownian motion and solving the Stokes-Einstein equation, which relates the particle size to the measured diffusion constant, as is known in the art.

For each sample, 3 measurements may be made and Z-average values may be reported as the particle size.

The one or more silicones may be in the form of a nanoemulsion. The nanoemulsion may comprise any silicone suitable for application to the skin and/or hair.

The one or more silicones may include in their molecular structure polar functional groups such as Si—OH (present in dimethiconols), primary amines, secondary amines, tertiary amines, and quaternary ammonium salts. The one or more silicones may be selected from the group consisting of aminosilicones, pendant quaternary ammonium silicones, terminal quaternary ammonium silicones, amino polyalkylene oxide silicones, quaternary ammonium polyalkylene oxide silicones, and amino morpholino silicones.

The one or more silicones may comprise:
(a) at least one aminosilicone corresponding to formula (V):

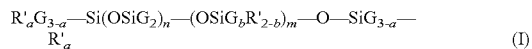
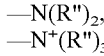

(I)

in which:
G is chosen from a hydrogen atom, a phenyl group, OH group, and $C_1$-$C_8$ alkyl groups, for example methyl,
a is an integer ranging from 0 to 3, and in one embodiment a is 0,
b is chosen from 0 and 1, and in one embodiment b is 1,
m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10;
R' is a monovalent group of formula —$C_qH_{2q}$L in which q is a number from 2 to 8 and L is an optionally quaternized amine group chosen from the groups:
—NR"—$CH_2$—$CH_2$—N'($R^1$)$_2$,
—N(R")$_2$,
—$N^+$(R")$_3$$A^-$,
—$N^+$H(R")$_2$$A^-$,
—$N^+_2$(R")$A^-$, and
—N(R")—$CH_2$—$CH_2$—$N^+$R"$H_2$$A^-$,
in which R" can be chosen from a hydrogen atom, phenyl groups, benzyl groups, and saturated monovalent hydrocarbon-based groups, such as for example an alkyl group comprising from 1 to 20 carbon atoms, and $A^-$ is chosen from halide ions such as, for example, fluoride, chloride, bromide and iodide.

The one or more silicones may include those corresponding to formula (1) wherein a=0, G=methyl, m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10; and L is —N($CH_3$)$_2$ or —$NH_2$, alternatively —$NH_2$.

Additional said at least one aminosilicone of the invention include:
(b) pendant quaternary ammonium silicones of formula (VII):

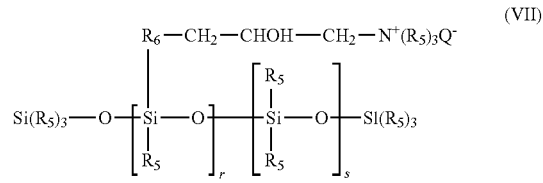

in which:
$R_5$ is chosen from monovalent hydrocarbon-based groups comprising from 1 to 18 carbon atoms, such as $C_1$-$C_{18}$ alkyl groups and $C_2$-$C_{18}$ alkenyl groups, for example methyl;
$R_6$ is chosen from divalent hydrocarbon-based groups, such as divalent $C_1$-$C_{18}$ alkylene groups and divalent $C_1$-$C_{18}$ alkylenoxy groups, for example $C_1$-$C_8$ alkylenoxy groups, wherein said $R_6$ is bonded to the Si by way of an SiC bond;
$Q^-$ is an anion that can be for example chosen from halide ions, such as chloride, and organic acid salts (such as acetate);

r is an average statistical value ranging from 2 to 20, such as from 2 to 8;
s is an average statistical value ranging from 20 to 200, such as from 20 to 50.

Such aminosilicones are described more particularly in U.S. Pat. No. 4,185,087, the disclosure of which is incorporated by reference herein.

A silicone which falls within this class is the silicone sold by the company Union Carbide under the name "Ucar Silicone ALE 56".

Further examples of said at least one aminosilicone include:

c) quaternary ammonium silicones of formula (VIIb):

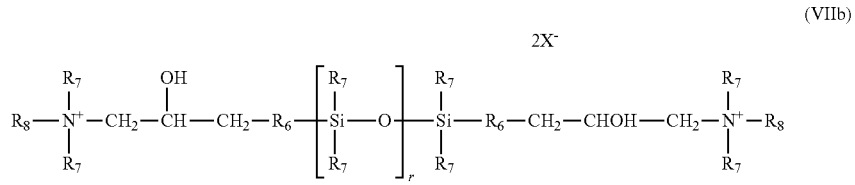

in which:
groups $R_7$, which may be identical or different, are each chosen from monovalent hydrocarbon-based groups comprising from 1 to 18 carbon atoms, such as $C_1$-$C_{18}$ alkyl groups, for example methyl, $C_2$-$C_{15}$ alkenyl groups, and rings comprising 5 or 6 carbon atoms;
$R_6$ is chosen from divalent hydrocarbon-based groups, such as divalent $C_1$-$C_{18}$ alkylene groups and divalent $C_1$-$C_{18}$alkylenoxy, for example $C_1$-$C_8$, group connected to the Si by an SiC bond;
$R_8$, which may be identical or different, represent a hydrogen atom, a monovalent hydrocarbon-based group comprising from 1 to 18 carbon atoms, and in particular a $C_1$-$C_{18}$ alkyl group, a $C_2$-$C_{18}$ alkenyl group or a group —$R_6$—$NHCOR_7$;
$X^-$ is an anion such as a halide ion, in particular chloride, or an organic acid salt (acetate, etc.); r represents an average statistical value from 2 to 200 and in particular from 5 to 100.

Such silicones are described, for example, in application EP-A-0 530 974, the disclosure of which is incorporated by reference herein.

Silicones falling within this class are the silicones sold by the company Eovnik under the names Abil Quat 3270, Abil Quat 3272, Abil Quat 3474 and Abil ME 45.

Further examples of said at least one aminosilicone include:
d) quaternary ammonium and polyalkylene oxide silicones wherein the quaternary nitrogen groups are located in the polysiloxane backbone, at the termini, or both.

Such silicones are described in PCT Publication No. WO 2002/010257, the disclosure of which is incorporated by reference herein.

Silicones falling within this class are the silicones sold by the company Momentive under the names Silsoft Q.

(e) Aminofunctional silicones having morpholino groups of formula (V):

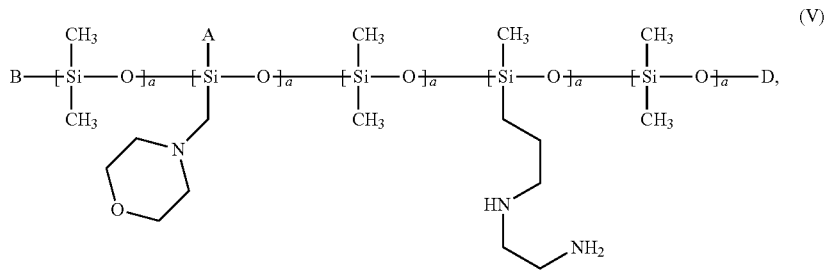

in which

A denotes a structural unit (I), (II), or (III) bound via —O—

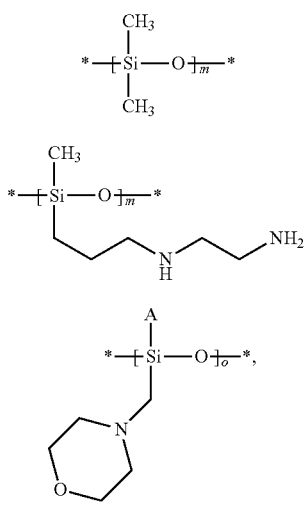

or an oligomeric or polymeric residue, bound via —O—, containing structural units of formulas (I), (II), or (III), or half of a connecting oxygen atom to a structural unit (III), or denotes —OH, \* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers between 0 and 1000, with the provision that a+b+c>0, m, n, and o denote integers between 1 and 1000.

Aminofunctional silicones of this kind bear the INCI name: Amodimethicone/Morpholinomethyl Silsesquioxane Copolymer. A particularly suitable amodimethicone is the product having the commercial name Wacker Belsil® ADM 8301E.

Examples of such silicones are available from the following suppliers:

offered by the company Dow Corning: Fluids: 2-8566, AP 6087, AP 6088, DC 8040 Fluid, fluid 8822A DC, DC 8803 & 8813 polymer, 7-6030, AP-8104, AP 8201; Emulsions: CE-8170 AF Micro Emulsion, 2-8177, 2-8194 Microemulsion, 9224 Emulsion, DC 1872 Emulsion, 939, 949, 959, DC 5-7113 Quat Microemulsion, DC 5-7070 Emulsion, DC CE-8810, CE 8401 Emulsion, CE 1619, Dow Corning Toray SS-3551, Dow Corning Toray SS-3552;

offered by the company Wacker: Wacker Belsil ADM 652, ADM 656, 1100, 1600, 1650 (fluids) ADM 6060 (linear amodimethicone) emulsion; ADM 6057 E (branched amodimethicone) emulsion; ADM 8020 VP (micro emulsion); SLM 28040 (micro emulsion); DM5500 emulsion;

offered by the Company Momentive: Silsoft 331, SF1708, SME 253 & 254 (emulsion), SM2125 (emulsion), SM 2658 (emulsion), Silsoft Q (emulsion)

offered by the company Shin-Etsu: KF-889, KF-8675, KF-8004, X-52-2265 (emulsion);

offered by the Company Siltech Silicones: Siltech E-2145, E-Siltech 2145-35;

offered by the company Evonik Industries: Abil T Quat 60th

Some non-limiting examples of aminosilicones include the compounds having the following INCI names: Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, Silicone Quaternium-22, Quaternium-80, as well as Silicone Quaternium-2 Panthenol Succinate and Silicone Quaternium-16/Glycidyl Dimethicone Crosspolymer.

The aminosilicones can be supplied in the form of a nanoemulsion and include MEM 9049, MEM 8177, MEM 0959, MEM 8194, SME 253, and Silsoft Q.

The one or more silicones may include dimethicones, and/or dimethiconols. The dimethiconols are hydroxyl terminated dimethylsilicones represented by the general chemical formulas

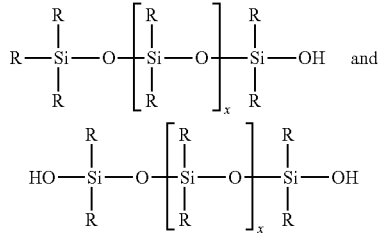

wherein R is an alkyl group (preferably R is methyl or ethyl, more preferably methyl) and x is an integer up to about 500, chosen to achieve the desired molecular weight. Commercial dimethiconols typically are sold as mixtures with dimethicone or cyclomethicone (e.g., Dow Corning® 1401, 1402, and 1403 fluids).

According to another aspect of the silicone emulsion, the emulsion further includes an anionic surfactant that participates in providing high internal phase viscosity emulsions having particle sizes in the range from about 30 nm to about 10 micron. The anionic surfactant is selected from organic sulfonic acids. Most common sulfonic acids used in the present process are alkylaryl sulfonic acid; alkylaryl polyoxyethylene sulphonic acid; alkyl sulfonic acid; and alkyl polyoxyethylene sulfonic acid. General formulas of the sulfonic acids are as shown below:

| | |
|---|---|
| R16C6H4SO3H | (I) |
| R16C6H4O(C2H4O)$m$SO$_3$H | (II) |
| R16SO3H | (III) |
| R16O(C2H4O)$m$SO$_3$H | (IV) |

Where R16, which may differ, is a monovalent hydrocarbon radical having at least 6 carbon atoms. Non-limiting examples of R16 include hexyl, octyl, decyl, dodecyl, cetyl, stearyl, myristyl, and oleyl. 'm' is an integer from 1 to 25. Exemplary anionic surfactants include but are not limited to octylbenzene sulfonic acid; dodecylbenzene sulfonic acid; cetylbenzene sulfonic acid; alpha-octyl sulfonic acid; alpha-dodecyl sulfonic acid; alpha-cetyl sulfonic acid; polyoxyethylene octylbenzene sulfonic acid; polyoxyethylene dodecylbenzene sulfonic acid; polyoxyethylene cetylbenzene sulfonic acid; polyoxyethylene octyl sulfonic acid; polyoxyethylene dodecyl sulfonic acid; and polyoxyethylene cetyl sulfonic acid. Generally, 1 to 15% anionic surfactant is used in the emulsion process. For example, 3-10% anionic surfactant can be used to obtain an optimum result. The silicone emulsion may further include an additional emulsifier together with the anionic surfactant, which along with the controlled temperature of emulsification and polymerization, facilitates making the emulsion in a simple and faster 5 way. Non-ionic emulsifiers having a hydrophilic lipophilic balance (HLB) value of 10 to 19 are suitable and include polyoxyalkylene alkyl ether, polyoxyalkylene alkylphenyl ethers and polyoxyalkylene sorbitan esters. Some useful emulsifiers having an HLB value of 10 to 19 include, but are not limited to, polyethylene glycol octyl ether; polyethylene glycol lauryl ether; polyethylene glycol tridecyl ether; polyethylene glycol cetyl ether; polyethylene glycol stearyl ether; polyethylene glycol nonylphenyl ether; polyethylene glycol dodecylphenyl ether; polyethylene glycol cetylphenyl ether; polyethylene glycol stearylphenyl ether; polyethylene glycol sorbitan mono stearate; and polyethylene glycol sorbitan mono oleate.

D. Water Miscible Solvent

The hair care composition comprises water-miscible solvent or combination of water-miscible solvent. The content of the water-miscible solvent is from about 0 wt % to about 15 wt %, from about 0.5 wt % to about 12 wt %, from about 1 wt % to about 10 wt %, from about 2 wt % to about 10 wt %. Suitable water miscible solvents include, but are not limited to, dipropylene glycol, tripropylene glycol, diethylene glycol, ethylene glycol, propylene glycol, glycerin, 1,3-propane diol, 2,2-propanediol, 1,2-butanediol, 1,3-butanediol, 1,4-butanediol, 2,3-butanediol, 2-methyl-2,4-pentanediol, and mixtures thereof. The hair care composition may comprise two or more water miscible solvents, wherein at least one of the solvents is dipropylene glycol.

The hair care compositions may have a pH in the range from about 2 to about 10, at 25° C. Alternatively, the hair care composition has a pH in the range from about 4 to about 7, which may help to solubilize minerals and redox metals already deposited on the hair. Thus, the hair care composition can also be effective toward washing out the existing minerals and redox metals deposits, which can reduce cuticle distortion and thereby reduce cuticle chipping and damage.

The hair care composition can also comprise a hydrotope or mixture of hydrotrope. Suitable hydrotrope include, but are not limited to alkali metal or ammonium salt of a lower alkyl benzene sulphonates such as Sodium Xylene Sulfonate (SXS), sodium cumene sulphonate, sodium toluene sulphonate and mixtures thereof.

E. Optional Ingredients

The hair care composition may further comprise one or more optional ingredients, including benefit agents Suitable benefit agents include, but are not limited to conditioning agents, cationic polymers silicone emulsions, anti-dandruff actives, gel networks, chelating agents, and, natural oils such as sun flower oil or castor oil. Additional suitable optional ingredients include but are not limited to perfumes, perfume microcapsules, colorants, particles, anti-microbials, foam busters, anti-static agents, rheology modifiers and thickeners, suspension materials and structurants, pH adjusting agents and buffers, preservatives, pearlescent agents, solvents, diluents, anti-oxidants, vitamins and combinations thereof.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

1. Non-Silicone Conditioning Agents

The conditioning agent of the hair care compositions described herein may also comprise at least one organic conditioning agents, either alone or in combination with other conditioning agents, such as the silicones described above. Non-limiting examples of organic conditioning agents are described below.

a. Hydrocarbon Oils

Suitable organic conditioning agents for use as conditioning agents in hair care compositions include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils can be from about $C_{12}$ to about $C_{19}$. Branched chain hydrocarbon oils, including hydrocarbon polymers, typically will contain more than 19 carbon atoms.

b. Polyolefins

Organic conditioning oils for use in the hair care compositions described herein also include liquid polyolefins, including liquid poly-α-olefins and/or hydrogenated liquid poly-α-olefins. Polyolefins for use herein are prepared by polymerization of $C_4$ to about $C_{14}$ olefinic monomers, and in one embodiment from about $C_6$ to about $C_{12}$.

c. Fatty Esters

Other suitable organic conditioning agents for use as a conditioning agent in the hair care compositions described herein include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.). Other oligomeric or polymeric esters, prepared from unsaturated glyceryl esters can also be used as conditioning materials.

d. Fluorinated Conditioning Compounds

Fluorinated compounds suitable for delivering conditioning to hair as organic conditioning agents include perfluoropolyethers, perfluorinated olefins, fluorine based specialty polymers that may be in a fluid or elastomer form similar to the silicone fluids previously described, and perfluorinated dimethicones.

e. Fatty Alcohols

Other suitable organic conditioning oils for use in the hair care compositions described herein include, but are not limited to, fatty alcohols having at least about 10 carbon atoms, about 10 to about 22 carbon atoms, and in one embodiment about 12 to about 16 carbon atoms.

f. Alkyl Glucosides and Alkyl Glucoside Derivatives

Suitable organic conditioning oils for use in the hair care compositions described herein include, but are not limited to, alkyl glucosides and alkyl glucoside derivatives. Specific non-limiting examples of suitable alkyl glucosides and alkyl glucoside derivatives include Glucam E-10, Glucam E-20, Glucam P-10, and Glucquat 125 commercially available from Amerchol.

g. Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M and mixtures thereof.

2. Emulsifiers

A variety of anionic and nonionic emulsifiers can be used in the hair care compositions. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

3. Chelating Agents

The hair care composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term include alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440.

Levels of the EDDS chelant in the hair care compositions can be as low as about 0.01 wt % or even as high as about 10 wt %, but above the higher level (i.e., 10 wt %) formulation and/or human safety concerns may arise. The level of the EDDS chelant may be at least about 0.05 wt %, at least about 0.1 wt %, at least about 0.25 wt %, at least about 0.5 wt %, at least about 1 wt %, or at least about 2 wt % of the hair care composition. Levels above about 4 wt % can be used but may not result in additional benefit.

4. Anti-Dandruff Actives

Anti-dandruff agents suitable for use in hair care compositions include pyridinethione salts, azoles (e.g., ketoconazole, econazole, and elubiol), selenium sulfide, particulate sulfur, salicylic acid, and mixtures thereof. A typical anti-dandruff agent is pyridinethione salt. Hair care compositions can also include a zinc-containing layered material. An example of a zinc-containing layered material can include zinc carbonate materials. Of these, zinc carbonate and pyridinethione salts (particularly zinc pyridinethione or "ZPT) are common in the composition, and often present together.

5. Aqueous Carrier

The hair care compositions can be in the form of pourable liquids (under ambient conditions). Such compositions will therefore typically comprise a carrier, which is present at a level of from about 40% to about 80%, alternatively from about 45% to about 75%, alternatively from about 50% to about 70%, by weight of the hair care composition. The carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

Carriers useful in the hair care compositions include water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

F. Product Form

The hair care compositions may be presented in typical hair care formulations. They may be in the form of solutions, dispersion, emulsions, powders, talcs, encapsulated, spheres, spongers, solid dosage forms, foams, and other delivery mechanisms. The compositions may be hair tonics, leave-on hair products such as treatment, and styling products, rinse-off hair products such as shampoos and personal cleansing products, and treatment products; and any other form that may be applied to hair.

The hair care composition in the form of a foam can have a density of from about 0.02 g/cm$^3$ to about 0.35 g/cm$^3$, alternatively from about 0.025 g/cm$^3$ to about 0.30 g/cm$^3$, and alternatively from about 0.03 g/cm$^3$ to about 0.25 g/cm$^3$.

G. Foam Dispenser

The composition can be stored and dispensed from an aerosol foam dispenser that may comprise a reservoir for holding the hair care composition. The reservoir may be made out of any suitable material selected from the group consisting of plastic, metal, alloy, laminate, and combinations thereof. The reservoir may be for one-time use. In an embodiment, the reservoir may be removable from the aerosol foam dispenser. Alternatively, the reservoir may be integrated with the aerosol foam dispenser. In an embodiment, there may be two or more reservoirs.

The reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

Alternatively, the hair care composition can be stored and dispensed from a mechanical foam dispenser. Non-limiting examples of suitable pump dispensers include those described in WO 2004/078903, WO 2004/078901, and WO 2005/078063 and may be supplied by Albea (60 Electric Ave., Thomaston, Conn. 06787 USA) or Rieke Packaging Systems (500 West Seventh St., Auburn, Ind. 46706).

H. Foaming Agent

The hair care composition described herein may comprise from about from about 1% to about 10% propellant, alternatively from about 2% to about 8% propellant, alternatively from about 2.5% to about 7% propellant, and alternatively from about 3% to about 6% propellant, by weight of the hair care composition.

The propellant may comprise one or more volatile materials, which in a gaseous state, may carry the other components of the hair care composition in particulate or droplet form. The propellant may have a boiling point within the range of from about −45° C. to about 5° C. The propellant may be liquefied when packaged in convention aerosol containers under pressure. The rapid boiling of the propellant upon leaving the aerosol foam dispenser may aid in the atomization of the other components of the hair care composition.

Aerosol propellants which may be employed in the aerosol composition may include the chemically-inert hydrocarbons such as propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, and mixtures thereof. The propellant may comprise hydrocarbons such as isobutane, propane, and butane—these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar. The foaming agent may comprise hydrofluoroolefins (HFOs).

Test Methods

A. Cone/Plate Viscosity Measurement

The viscosities of the examples are measured by a Cone/Plate Controlled Stress Brookfield Rheometer R/S Plus, by Brookfield Engineering Laboratories, Stoughton, Mass. The cone used (Spindle C-75-1) has a diameter of 75 mm and 1° angle. The viscosity is determined using a steady state flow experiment at constant shear rate of $2\ s^{-1}$ and at temperature of 26.5° C. The sample size is 2.5 ml and the total measurement reading time is 3 minutes.

B. Hair Wet Feel Friction measurement (final rinse friction and initial rinse friction):

A switch of 4 grams general population hair at 8 inches length is used for the measurement. Water temperature is set at 100° F., hardness is 7 grain per gallon, and flow rate is 1.6 liter per minute. For shampoos in liquid form, 0.2 ml of a liquid shampoo is applied on the hair switch in a zigzag pattern uniformly to cover the entire hair length, using a syringe. For shampoo in aerosol foam form, foam shampoo is dispensed to a weighing pan on a balance. 0.2 grams of foam shampoo is taken out from weighing pan and applied on the hair switch uniformly to cover the entire hair length via a spatula. The hair switch is then 1st lathered for 30 seconds, rinse with water for 30 seconds, and 2nd lathered for 30 seconds. Water flow rate is then reduced to 0.2 liter per minute. The hair switch is sandwiched with a clamp under 1800 gram of force and pulled through the entire length while the water is running at the low flow rate. The pull time is 30 second. Friction is measured with a friction analyzer with a load cell of 5 kg. Repeat the pull under rinse for total of 21 times. Total 21 friction values are collected. The final rinse friction is the average friction of the last 7 points and initial rinse friction is the average of the initial 7 points. The delta final to initial is calculated by subtracting the final rinse friction from the initial rinse friction.

C. Foam Density & Foam Volume

Foam density is measured by placing a 100 ml beaker onto a mass balance, tarring the mass of the beaker and then dispensing product from the aerosol container into the 100 ml beaker until the volume of the foam is above the rim of the vessel. The foam is made level with the top of the beaker by scraping a spatula across it within 10 seconds of dispensing the foam above the rim of the vessel. The resulting mass of the 100 ml of foam is then divided by the volume (100) to determine the foam density in units of g/ml.

Foam volume is measured by placing a weigh boat onto a mass balance, tarring the mass of the weigh boat and then dispensing the desired amount of product from the aerosol container. The grams of foam dispensed is determined and then divided by the density of foam as determined from the Foam Density methodology to reach a volume of foam in ml or $cm^3$.

EXAMPLES

The following are non-limiting examples of the hair care composition described herein. The examples were prepared by conventional formulation and mixing techniques. It will be appreciated that other modifications of the present invention within the skill of those in the shampoo formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

TABLE 2

Comparative Examples of Shampoo Compositions in Foam Form

|  | Comp. Ex. 1 | Comp. Ex. 2 | Comp. Ex. 3 | Comp. Ex. 4 | Comp. Ex. 5 |
| --- | --- | --- | --- | --- | --- |
| Viscosity (cps) | 2593 | 4095 | 1927 | 3989 | 4647 |
| Final Rinse Friction (gf) | 1788 | 1694 | 1578 | 1656 | 1405 |
| Delta final to initial | 501 | 340 | 431 | 435 | 269 |
| Sodium laureth-1-sulfate SLE1S[1] | 18 | 18 | 18 | 18 | 18 |
| Branched sodium trideceth-2-sulfate ST2S[2] | 8 | 8 | 8 | 8 | 8 |
| Cocoamidopropyl betaine[3] | 2 | 2 | 2 | 2 | 2 |
| Sodium Lauroamphoacetate [4] | 2 | 2 | 2 | 2 | 2 |
| Fragrance | 2.4 | 2.4 | 2.4 | 2.4 | 2.4 |
| Dipropylene glycol | 4 | 4 | 4 | 4 | 4 |
| Guar, Hydroxylpropyl Trimonium Chloride, Jaguar C500[5] | 0.4 | 0.8 | 0.4 | — | — |
| Guar, Hydroxylpropyl Trimonium Chloride, n-Hance 3271[6] | — | — | — | 0.8 | 0.4 |
| Guar, Hydroxylpropyl Trimonium Chloride, n-Hance CG17[7] | — | — | — | — | 0.2 |
| Polyquaternium-6[8] | — | — | — | — | 0.4 |
| Silicone Emulsion DC1872[10] | — | — | 2 | — | — |
| PEO N-12K[11] | — | — | — | — | 0.2 |
| HFO[15] | 7.0 | 7.0 | 7.0 | 7.0 | 7.0 |
| Preservatives, pH adjusters | Adjust as needed, up to 1% | | | | |
| Water | Q.S. | Q.S. | Q.S. | Q.S. | Q.S. |

TABLE 3

Examples of Shampoo Compositions in Foam Form

| | Ex. A | Ex. B | Ex. C | Ex. D | Ex. E | Ex. F | Ex. G | Ex. H | Ex. I |
|---|---|---|---|---|---|---|---|---|---|
| Viscosity (cps) | 4203 | 4933 | 2575 | 3118 | 3720 | 3095 | 2241 | 4684 | 4674 |
| Final Rinse Friction (gf) | 1314 | 1197 | 1239 | 1091 | 1254 | 1143 | 1294 | 1222 | 1106 |
| Delta final to initial | 272 | 231 | 238 | 148 | 236 | 181 | 271 | 194 | 138 |
| Sodium laureth-1-sulfate SLE1S[1] | 18 | 18 | 18 | 18 | 18 | 18 | 18 | 18 | 18 |
| Branched sodium trideceth-2-sulfate ST2S[2] | 8 | 8 | 8 | 8 | 8 | 8 | 8 | 8 | 8 |
| Cocoamidopropyl betaine[3] | 2 | 2 | 2 | 2 | 2 | 2 | 2 | 2 | 2 |
| Sodium Lauroamphoacetate [4] | 2 | 2 | 2 | 2 | 2 | 2 | 2 | 2 | 2 |
| Fragrance | 2.4 | 2.4 | 2.4 | 2.4 | 2.4 | 2.4 | 2.4 | 2.4 | 2.4 |
| Dipropylene glycol | 4 | 4 | 4 | 4 | 4 | 4 | 4 | 4 | 4 |
| Guar, Hydroxylpropyl Trimonium Chloride, n-Hance 3271[6] | 0.8 | 0.8 | 0.4 | 0.4 | 0.8 | 0.8 | 0.4 | 0.4 | 0.4 |
| Guar, Hydroxylpropyl Trimonium Chloride, n-Hance CG17[7] | — | — | — | — | — | — | — | 0.2 | 0.2 |
| Polyquaternium-6[8] | 0.4 | 0.4 | 0.4 | 0.4 | 0.4 | 0.4 | 0.4 | 0.4 | 0.4 |
| Silicone Emulsion DM5500[9] | 2 | 4 | 2 | 4 | — | — | — | — | — |
| Silicone Emulsion DC1872[10] | — | — | — | — | 2 | 4 | 2 | 2 | 4 |
| PEO N-12K[11] | — | — | 0.2 | 0.2 | 0.2 | 0.2 | 0.2 | 0.2 | 0.2 |
| HFO[15] | 7.0 | 7.0 | 7.0 | 7.0 | 7.0 | 7.0 | 7.0 | 7.0 | 7.0 |
| Preservatives, pH adjusters | colspan Adjust as needed, up to 1% | | | | | | | | |
| Water | Q.S. | Q.S. | Q.S. | Q.S. | Q.S. | Q.S. | Q.S. | Q.S. | Q.S. |

Examples A to I may be preferred by consumers over Comparative Examples 1-5 because they can provide a more optimal in-use wet feel that can suggest to the consumer that the hair is both clean and conditioned. Compositions with optimal in-use wet feel have relatively low final rinse friction in combination with a relatively high delta final to initial. The final rinse friction of Examples A-I ranges from 1091 to 1314 gf. This is lower than the final rinse friction for the Comparative Examples 1-5, which range from 1405 to 1788 gf. The delta final to initial for Examples A-I ranges from 138-272 gf.

TABLE 4

Comparative Examples of Shampoo Compositions in Compact Liquid Form

| | Comp. Ex. 6 | Comp. Ex. 7 | Comp. Ex. 8 | Comp. Ex. 9 | Comp. Ex. 10 | Comp. Ex. 11 | Comp. Ex. 12 | Comp. Ex. 13 |
|---|---|---|---|---|---|---|---|---|
| Viscosity (cps) | 2593 | 4095 | 1927 | 3989 | 4647 | 1949 | 1625 | 2046 |
| Final Rinse Friction (gf) | 1839 | 1828 | 1588 | 1873 | 1480 | 2053 | 1805 | 1809 |
| Delta final to initial | 397 | 386 | 343 | 388 | 289 | 410 | 496 | 462 |
| Sodium laureth-1-sulfate SLE1S[1] | 18 | 18 | 18 | 18 | 18 | — | 13 | 26 |
| Branched sodium trideceth-2-sulfate ST2S[2] | 8 | 8 | 8 | 8 | 8 | — | 13 | — |
| Cocoamidopropyl betaine[3] | 2 | 2 | 2 | 2 | 2 | — | 4 | 4 |
| Sodium Lauroamphoacetate [4] | 2 | 2 | 2 | 2 | 2 | — | — | — |
| Disodium Laureth sulfosuccinate[11] | — | — | — | — | — | 10 | — | — |
| Coco Glucoside[12] | — | — | — | — | — | 9.8 | — | — |
| Sodium cocoamphoacetate[13] | — | — | — | — | — | 11.85 | — | — |
| Fragrance | 2.4 | 2.4 | 2.4 | 2.4 | 2.4 | 2.4 | 2.4 | 2.4 |
| Dipropylene glycol | 4 | 4 | 4 | 4 | 4 | 4 | 4 | 4 |
| Guar, Hydroxylpropyl Trimonium Chloride, Jaguar C500[14] | 0.4 | 0.8 | 0.4 | — | — | 0.4 | 0.4 | 0.4 |

TABLE 4-continued

Comparative Examples of Shampoo Compositions in Compact Liquid Form

| | Comp. Ex. 6 | Comp. Ex. 7 | Comp. Ex. 8 | Comp. Ex. 9 | Comp. Ex. 10 | Comp. Ex. 11 | Comp. Ex. 12 | Comp. Ex. 13 |
|---|---|---|---|---|---|---|---|---|
| Guar, Hydroxylpropyl Trimonium Chloride, n-Hance 3271[6] | — | — | — | 0.8 | 0.4 | — | — | — |
| Guar, Hydroxylpropyl Trimonium Chloride, n-Hance CG17[7] | — | — | — | — | 0.2 | — | — | — |
| Polyquaternium-6[8] | — | — | — | — | 0.4 | — | — | — |
| Silicone Emulsion DC1872[10] | — | — | 2 | — | — | — | — | — |
| PEO N-12K[11] | — | — | — | — | 0.2 | — | — | — |
| Preservatives, pH adjusters | Adjust as needed, up to 1% | | | | | | | |
| Water | Q.S. | Q.S. | Q.S. | Q.S. | Q.S. | Q.S. | Q.S. | Q.S. |

TABLE 5

Examples of Shampoo Compositions in Compact Liquid Form

| | Ex. J | Ex. K | Ex. L | Ex. M | Ex. N | Ex. O | Ex. P | Ex. Q | Ex. R | Ex. S | Ex. T |
|---|---|---|---|---|---|---|---|---|---|---|---|
| Viscosity (cps) | 4203 | 4933 | 2575 | 3118 | 3720 | 3095 | 2241 | 4674 | 2164 | 2102 | 2102 |
| Final Rinse Friction (gf) | 1343 | 1302 | 1324 | 1083 | 1304 | 1297 | 1324 | 1140 | 1031 | 1179 | 1278 |
| Delta final to initial | 280 | 302 | 287 | 165 | 288 | 266 | 286 | 204 | 235 | 264 | 314 |
| Sodium laureth-1-sulfate SLE1S[1] | 18 | 18 | 18 | 18 | 18 | 18 | 18 | 18 | — | 13 | 26 |
| Branched sodium trideceth-2-sulfate ST2S[2] | 8 | 8 | 8 | 8 | 8 | 8 | 8 | 8 | — | 13 | — |
| Cocoamidopropyl betaine[3] | 2 | 2 | 2 | 2 | 2 | 2 | 2 | 2 | — | 4 | 4 |
| Sodium Lauroamphoacetate[4] | 2 | 2 | 2 | 2 | 2 | 2 | 2 | 2 | — | — | — |
| Disodium Laureth sulfosuccinate[11] | — | — | — | — | — | — | — | — | 10 | — | — |
| Coco Glucoside[12] | — | — | — | — | — | — | — | — | 9.8 | — | — |
| Sodium cocoamphoacetate[13] | — | — | — | — | — | — | — | — | 11.85 | — | — |
| Fragrance | 2.4 | 2.4 | 2.4 | 2.4 | 2.4 | 2.4 | 2.4 | 2.4 | 2.4 | 2.4 | 2.4 |
| Dipropylene glycol | 4 | 4 | 4 | 4 | 4 | 4 | 4 | 4 | 4 | 4 | 4 |
| Guar, Hydroxylpropyl Trimonium Chloride, Jaguar C500[14] | — | — | — | — | — | — | — | — | 0.4 | 0.4 | 0.4 |
| Guar, Hydroxylpropyl Trimonium Chloride, n-Hance 3271[6] | 0.8 | 0.8 | 0.4 | 0.4 | 0.8 | 0.8 | 0.4 | 0.4 | — | — | — |
| Guar, Hydroxylpropyl Trimonium Chloride, n-Hance CG17[7] | — | — | — | — | — | — | — | 0.2 | — | — | — |
| Polyquaternium-6[8] | 0.4 | 0.4 | 0.4 | 0.4 | 0.4 | 0.4 | 0.4 | 0.4 | 0.4 | 0.4 | 0.4 |
| Silicone Emulsion DM5500[9] | 2 | 4 | 2 | 4 | — | — | — | — | 4 | 4 | 4 |
| Silicone Emulsion DC1872[10] | — | — | — | — | 2 | 4 | 2 | 4 | — | — | — |

TABLE 5-continued

Examples of Shampoo Compositions in Compact Liquid Form

| | Ex. J | Ex. K | Ex. L | Ex. M | Ex. N | Ex. O | Ex. P | Ex. Q | Ex. R | Ex. S | Ex. T |
|---|---|---|---|---|---|---|---|---|---|---|---|
| PEO N-12K[11] | — | — | 0.2 | 0.2 | 0.2 | 0.2 | 0.2 | 0.2 | — | — | — |
| Preservatives, pH adjusters | | | | | Adjust as needed, up to 1% | | | | | | |
| Water | Q.S. | Q.S. | Q.S. | Q.S. | Q.S. | Q.S. | Q.S. | Q.S. | Q.S. | Q.S. | Q.S. |

[1]Sodium Laureth (1 molar ethylene oxide) sulfate at 70% active, supplier: Stephan Co
[2]Sodium Tridecyl Ether Sulfate (2 molar ethylene oxide), Stepan ST2S-65 (Steol-TD 402 65) 65% active, supplier: Stephan Co
[3]Tegobetaine F-B, 30% active, supplier: Goldschmidt Chemical
[4]NaLaa (Miranol Ultra L32) at 32% active level, supplier: Solvay
5. Jaguar ® C500, MW of 500,000, CD of 0.7, from Solvay
[6]N-Hance 3271, MW of 500,000, CD of 0.7, from Ashland
[7]N-Hance CG17, MW of 1, 600,000, CD of 1.0, from Ashland
[8]Polyquaternium 6, PolyDADMAC, MW of 150,000, CD of 6.2, trade name: Mirapol ® 100s, 31.5% active, from Solvay
[9]DM5500 silicone emulsion (dimethiconol) with an average particle size of 120 nm, from Wacker
[10]DC 1872 silicone emulsion (dimethiconol) with an average particle size of 30 nm, from Dow Corning
[11]POLYOX WSR N-12K, polyethylene oxide, MW of 1,000,000, from Dow.
[12]Coco Glucoside, Plantaren 818 UP, C8-16 fatty alcohol glucoside, 52% active, from BASF
[13]Sodium Cocoamphoacetate (NaCaa), Dehyton MC, 39% active, from BASF
[14]Jaguar ® C500, MW of 500,000, CD of 0.7, from Solvay
[15]Hydrofluoroolefins (HFO-1234ze), from Honey well Examples J to T may be preferred by consumers over Comparative Examples 6-13 because they can provide a more optimal in-use wet feel. The final rinse friction for Examples J-T range from 1031-1343 gf. This is significantly lower than the wet feel friction for the stable Comparative Examples 6-13, which range from 1480 to 2053. The delta final to initial for Examples J-T range from 165-314 gf.

Combinations:

A. A hair care composition comprising:
  a. from about 20% to about 45%, by weight, of a detersive surfactant;
  b. from about 0.01% to about 2.5%, by weight, of a cationic synthetic polymer comprising a homopolymer and/or a copolymer, charge density from about 2 to about 10 meq/g, and a molecular weight from about 1,000 g/mol to about 2,000,000 g/mol;
  c. from about 0.01% to about 2.5%, by weight, of a cationic guar polymer comprising a molecular weight of from about 50,000 g/mol to about 2,500,000 g/mol and charge density from about 0.1 meq/g to about 2.5 meq/g;
  d. from about 0.5% to about 10%, by weight, of silicone wherein the silicone comprises a plurality of particles wherein the average particle size is from about 1 nm to about 500 nm.

B. A hair care composition comprising:
  a. from about 20% to about 45%, by weight, of a detersive surfactant;
  b. from about 0.01% to about 2.5%, by weight, of a cationic synthetic polymer comprising a homopolymer and/or a copolymer, charge density from about 2 to about 10 meq/g, and a molecular weight from about 1,000 g/mol to about 2,000,000 g/mol;
  c. from about 0.01% to about 2.5%, by weight, of a cationic guar polymer comprising a molecular weight of from about 50,000 g/mol to about 2,500,000 g/mol and charge density from about 0.1 meq/g to about 2.5 meq/g;
  d. from about 0.1% to about 8%, by weight, of silicone wherein the silicone comprises a plurality of particles wherein the average particle size is from about 1 nm to about 500 nm;
  wherein the hair care composition produces a final rinse friction of from about 1000 gf to about 1700 gf; and
  wherein the hair care composition produces a delta final to initial of at least 125 gf.

C. The hair care composition according to Paragraphs A-B, wherein the composition comprises from about 0.15% to about 1.5%, alternatively from about 0.3% to about 0.9%, by weight, of the cationic guar polymer.

D. The hair care composition according to Paragraphs A-C, wherein the composition comprises from about 0.1% to about 1.6%, alternatively from about 0.2% to about 1.2%, by weight, of the cationic synthetic polymer.

E. The hair care composition according to Paragraphs A-D, wherein the composition comprises from about 0.05% to about 0.8%, by weight, of the cationic synthetic polymer.

F. The hair care composition according to Paragraphs A-E, wherein the composition comprises from about 1% to about 7% silicone, alternatively from about 1.5% to about 6% silicone.

G. The hair care composition according to Paragraphs A-F, wherein the silicone comprises a plurality of particles wherein the average particle size is from about 1 nm to about 400 nm, alternatively from about 5 nm to about 300 nm, alternatively from about 10 nm to about 250 nm, alternatively from about 20 nm to about 200 nm.

H. The hair care composition according to Paragraphs A-G, wherein the cationic synthetic polymer has the following structure

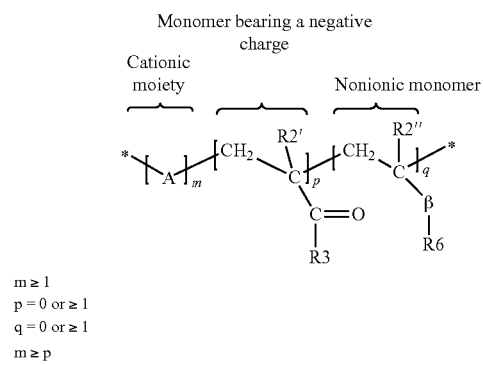

$m \geq 1$
$p = 0$ or $\geq 1$
$q = 0$ or $\geq 1$
$m \geq p$ where A, may be one or more of the following cationic moieties:

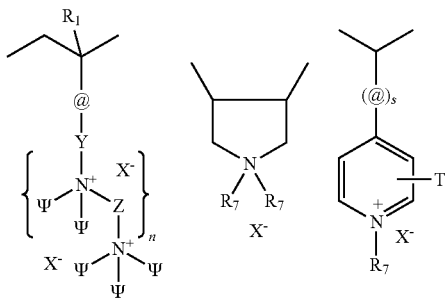

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl arylox;
where Z=C1-C22 alkyl, alkyloxy, aryl or aryloxy;
where R1=H, C1-C4 linear or branched alkyl;
where s=0 or 1, n=0 or $\geq 1$;
where T and R7=C1-C22 alkyl; and
where X-=halogen, hydroxide, alkoxide, sulfate or alkylsulfate.

Where the monomer bearing a negative charge is defined by R2'=H, C1-C4 linear or branched alkyl and R3 as:

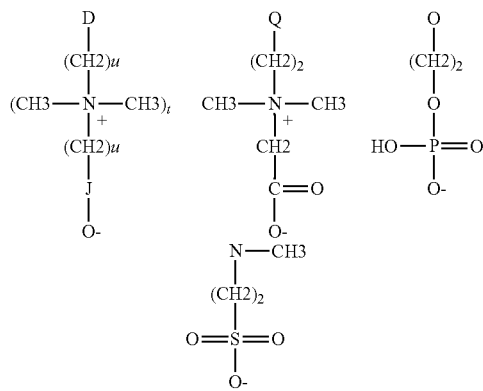

where D=O, N, or S;
where Q=NH$_2$ or O;
where u=1-6;
where t=0-1; and
where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as

and
where G' and G" are, independently of one another, O, S or N—H and L=0 or 1.

I. The hair care composition according to Paragraph H, wherein the cationic synthetic polymer is selected from the group consisting of homopolymer polydiallyldimethylammonium chloride, copolymer polydiallyldimethylammonium chloride, and combinations thereof.

J. The hair care composition according to Paragraph I, wherein the cationic synthetic polymer comprises polydiallyldimethylammonium chloride.

K. The hair care composition of according to Paragraphs A-J wherein the composition has a liquid phase viscosity of about 1 centipoise (cP) to about 15,000 cP, alternatively from about 10 cP to about 12,000 cP, alternatively from about 20 cP to about 10,000 cP, alternatively from about 50 cP to about 8,000 cP, alternatively from about 100 cP to about 5000 cP, alternatively from about 250 cP to about 3000 cP, alternatively from about 500 cP to about 2500 cP.

L. The hair care composition according to Paragraphs A-K, wherein said hair care composition is dispensed as a foam.

M. The hair care composition according to Paragraph L, wherein the density of the foam is from about 0.01 g/cm$^3$ to about 0.50 g/cm$^3$, alternatively from about 0.02 g/cm$^3$ to about 0.40 g/cm$^3$, alternatively from about 0.03 g/cm$^3$ to about 0.35 g/cm$^3$.

N. The hair care composition according to Paragraphs L-M, further comprising from about 1 to 15% of a foaming agent.

O. The hair care composition hair care composition according to Paragraphs L-N, wherein the foaming agent is selected from the group consisting of hydrocarbons, halogenated hydrocarbons, and combinations thereof.

P. The hair care composition according to Paragraphs L-N, wherein the foaming agent is selected from the group consisting of propane, n-butane, isobutane, cyclopropane, and combinations thereof.

Q. The hair care composition according to Paragraphs L-N, wherein the foaming agent comprises hydrofluroolefin (HFO).

R. The hair care composition according to Paragraphs A-Q, wherein the composition has a pH of from about 5 to about 7.

S. The hair care composition according to Paragraphs A-R, further comprising an anti-dandruff active.

T. The hair care composition according to Paragraphs A-S, wherein the silicone is selected from the group consisting of aminosilicones, pendant quaternary ammonium silicones, terminal quaternary ammonium silicones, amino polyalkylene oxide silicones, quaternary ammonium polyalkylene oxide silicones, amino morpholino silicones, and combinations thereof.

U. The hair care composition according to Paragraphs A-T, wherein the molecular weight of the cationic synthetic polymer is from about 6,000 g/mol to about 1.5 million g/mol, alternatively from about 8,000 g/mol to about 1.4 million g/mol, alternatively from about 10,000 g/mol to about 1.2 million g/mol, alternatively from about 25,000 g/mol to about 750,000 g/mol, alternatively from about 50,000 g/mol to about 500,000 g/mol, alternatively from about 100,000 g/mol to about 200,000 g/mol.

V. The hair care composition according to Paragraphs A-U, wherein the molecular weight of the cationic guar polymer is from about 150,000 g/mol to about 2 million g/mol, alternatively from about 300,000 g/mol to about 1.8 million g/mol, alternatively from about 400,000 g/mol to about 1.7 million g/mol, alternatively from about 500,000 g/mol to about 1.6 million g/mol.

W. The hair care composition according to Paragraphs A-V, wherein the charge density of the cationic guar polymer is from from about 0.2 meq/g to about 2.2 meg/g, alternatively from about 0.4 meq/g to about 1.9 meg/g, alternatively from about 0.5 meq/g to about 1.8 meg/g, alternatively from about 0.6 meq/g to about 1.3 meg/g, alternatively from about 0.7 meq/g to about 1.0 meg/g.

X. The hair care composition according to Paragraphs A-W, wherein the charge density of the cationic synthetic polymer is from about 2.5 meq/g to about 8 meg/g, alternatively from about 3.5 meq/g to about 7.5 meg/g, alternatively from about 4 meq/g to about 7 meg/g.

Y. The hair care composition according to Paragraphs A-X, wherein the hair care composition produces a final rinse friction of from about 1050 gf to about 1600 gf, alternatively from about 1025 gf to about 1400 gf.

Z. The hair care composition according to Paragraphs A-Y, wherein the hair care composition produces a final rinse friction less than 1400, alternatively less than 1350 gf.

AA. The hair care composition according to Paragraphs A-Z, wherein the hair care composition produces a delta final to initial of from about 150 gf to about 450-gf, alternatively about 175 gf to about 350 gf, alternatively from about 200 gf to about 300 gf.

BB. The hair care composition according to Paragraphs A-AA, wherein the hair care composition produces a delta final to initial of at least 150 gf, alternatively at least about 200 gf.

CC. A method of treating hair, the method comprising:
  a. applying to the hair the hair care composition according to Paragraphs A-BB, wherein the hair care composition is dispensed from an aerosol foam dispenser as a dosage of foam;
  b. rinsing the hair care composition;
  c. optionally applying to the hair a second hair care composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A method of treating hair, the method comprising:
   a. providing an aerosol foam dispenser containing from about 1% to about 15% foaming agent and a hair care composition, wherein the hair care composition is a compact liquid hair care composition comprising:
      i. from about 20% to about 45%, by weight, of a detersive surfactant system comprising:
         1. from about 15% to about 36%, by weight of the hair care composition, of an anionic surfactant;
         2. from about 1% to about 10%, by weight of the hair care composition, of a zwitterionic surfactant;
      ii. from about 0.2% to about 2.5%, by weight, of a cationic synthetic polymer comprising a homopolymer and/or a copolymer, charge density from about 2 to about 10 meq/g, and a molecular weight from about 1,000 g/mol to about 2,000,000 g/mol;
      iii. from about 0.4% to about 1.5%, by weight, of a cationic guar polymer comprising a molecular weight of from about 50,000 g/mol to about 2,500,000 g/mol and charge density from about 0.1 meq/g to about 2.5 meq/g;
      iv. from about 1.5% to about 6%, by weight, of a silicone selected from the group consisting of:
         hydroxyl terminated dimethylsilicones having one of the following structures:

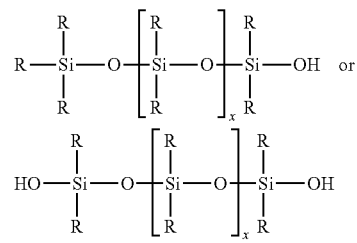

wherein R is an alkyl group and x is an integer up to about 500,
aminosilicones having the following formula:

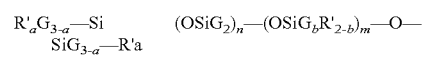

G is selected from the group consisting of a hydrogen atom, a phenyl group, an OH group, and $C_1$-$C_8$ alkyl groups, and combinations thereof;

a is an integer ranging from 0 to 3, b is selected from the group consisting of 0 and 1, m and n are numbers such that the sum (n+m) is from 1 to 2000, R' is a monovalent group of formula —$C_qH_{2q}L$ in which q is a number from 2 to 8 and L is an optionally quaternized amine group chosen from the groups:

—NR″—$CH_2$—$CH_2$—N′($R^1$)$_2$,

—N(R″)$_2$,

—$N^+$(R″)$_3$$A^-$,

—$N^+$H(R″)$_2$$A^-$,

—$N^+_2$(R″)$A^-$, and

—N(R″)—$CH_2$—$CH_2$—$N^+$R″$H_2$$A^-$, in which R″ can comprise a hydrogen atom, phenyl groups, benzyl groups, and saturated monovalent hydrocarbon-based groups, and combinations thereof, and $A^-$ is a halide ions selected from the group consisting of fluoride, chloride, bromide and iodide, and combinations thereof, and combinations thereof;

wherein the silicone comprises a plurality of particles having an average particle size is from about 1 nm to about 500 nm;

b. applying to a user's hair the hair care composition wherein the hair care composition is dispensed from the aerosol foam dispenser as a dosage of foam;

c. rinsing the hair care composition from the hair;

d. optionally applying to the hair a second hair care composition.

2. The method of claim 1 wherein the silicone comprises a plurality of particles wherein the average particle size is from about 20 nm to about 200 nm.

3. The method of claim 1 wherein the cationic synthetic polymer has the following structure Monomer bearing a negative charge

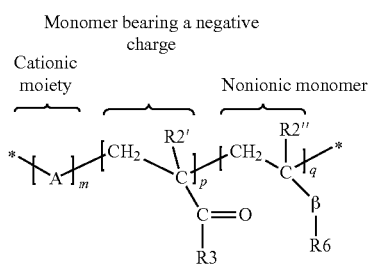

$m \geq 1$
$p = 0$ or $\geq 1$
$q = 0$ or $\geq 1$
$m \geq p$ where A, may be one or more of the following cationic moieties:

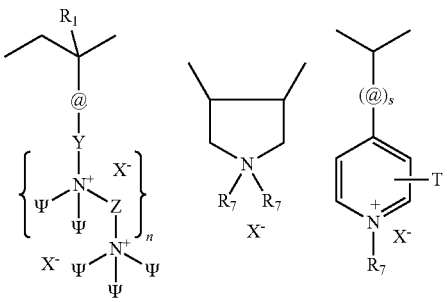

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl arylox;
where Z=C1-C22 alkyl, alkyloxy, aryl or aryloxy;
where R1=H, C1-C4 linear or branched alkyl;
where s=0 or 1, n=0 or 1;
where T and R7=C1-C22 alkyl; and
where X-=halogen, hydroxide, alkoxide, sulfate or alkylsulfate.

Where the monomer bearing a negative charge is defined by R2'=H, C1-C4 linear or branched alkyl and R3 as:

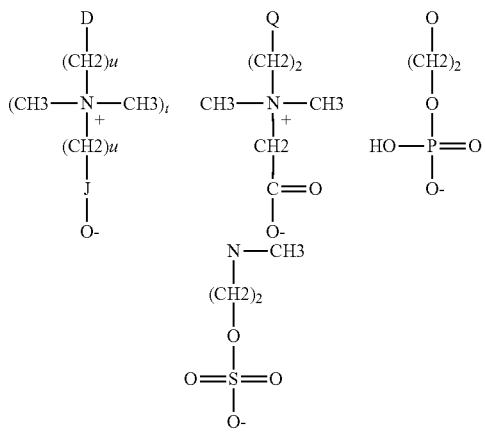

where D=O, N, or S;
where Q=$NH_2$ or O;
where u=1-6;
where t=0-1; and
where J=oxygenated functional group containing the following elements P, S, C.

Where the nonionic monomer is defined by R2″=H, C1-C4 linear or branched alkyl, R6=linear or branched alkyl, alkyl aryl, aryl oxy, alkyloxy, alkylaryl oxy and β is defined as

and
where G' and G″ are, independently of one another, O, S or N—H and L=0 or 1.

4. The method of claim 3 wherein the cationic synthetic polymer is selected from the group consisting of homopolymer polydiallyldimethylammonium chloride, copolymer polydiallyldimethylammonium chloride, and combinations thereof.

5. The method of claim 1 wherein the composition has a liquid phase viscosity of from about 5 centipoise to about 5000 centipoise.

6. The method of claim 1, wherein wherein the foaming agent is selected from the group consisting of propane, n-butane, isobutane, cyclopropane, and combinations thereof.

7. The method of claim 1, wherein wherein the foaming agent comprises hydrofluroolefin (HFO).

8. The method of claim 1 wherein the dosage of foam comprises a density from about 0.03 g/cm$^3$ to about 0.35 g/cm$^3$.

9. The method of claim 1 wherein
   wherein the hair comprises a final rinse friction of from about 1000 gf to about 1700 gf; and
   wherein the hair comprises a delta final to initial of at least 125 gf.

10. The method of claim 1 wherein the hair comprises a final rinse friction of from about 1025 gf to about 1400 gf.

11. The method of claim 1 wherein the hair comprises a delta final to initial of at least about 200 gf.

12. The method of claim 1 wherein the hair comprises a delta final to initial of from about 200 gf to about 300 gf.

13. The method of claim 1 wherein the composition comprises from about 0.4% to about 0.8%, by weight, of the cationic guar polymer.

14. The method of claim 1 wherein the cationic synthetic polymer comprises polydiallyldimethylammonium chloride.

\* \* \* \* \*